United States Patent
Gold et al.

(10) Patent No.: US 12,390,625 B2
(45) Date of Patent: Aug. 19, 2025

(54) NASAL DRUG DELIVERY SYSTEM

(71) Applicant: The Board of Trustees of The Leland Stanford Junior University, Stanford, CA (US)

(72) Inventors: Adam Gold, Mountain View, CA (US); Ashley Seehusen, Mountain View, CA (US); Jonathan Toma, Menlo Park, CA (US); Shira Koss, Palo Alto, CA (US)

(73) Assignee: The Board of Trustees of The Leland Stanford Junior University, Stanford, CA (US)

(*) Notice: Subject to any disclaimer, the term of this patent is extended or adjusted under 35 U.S.C. 154(b) by 651 days.

(21) Appl. No.: 17/476,334

(22) Filed: Sep. 15, 2021

(65) Prior Publication Data

US 2022/0032022 A1 Feb. 3, 2022

Related U.S. Application Data

(63) Continuation of application No. PCT/US2020/023826, filed on Mar. 20, 2020.

(60) Provisional application No. 62/915,371, filed on Oct. 15, 2019, provisional application No. 62/862,562, filed on Jun. 17, 2019, provisional application No. 62/825,668, filed on Mar. 28, 2019.

(51) Int. Cl.
*A61M 31/00* (2006.01)

(52) U.S. Cl.
CPC ....... *A61M 31/00* (2013.01); *A61M 2202/048* (2013.01); *A61M 2210/0618* (2013.01); *A61M 2210/0681* (2013.01)

(58) Field of Classification Search
CPC .. A61M 15/08; A61M 15/0021; A61M 11/008; A61M 11/007; A61M 11/006; A61M 2210/0618; A61M 2210/0681; A61M 31/00
See application file for complete search history.

(56) References Cited

U.S. PATENT DOCUMENTS

| 7,231,919 | B2 | 6/2007 | Giroux | |
| 11,172,807 | B2* | 11/2021 | Okazaki | A61B 1/00154 |
| 2010/0057048 | A1* | 3/2010 | Eldredge | A61B 17/24 |
| | | | | 604/528 |
| 2011/0152838 | A1 | 6/2011 | Xia | |

(Continued)

FOREIGN PATENT DOCUMENTS

| WO | WO 2000/053252 | 9/2000 |
| WO | WO 2007/093791 | 8/2007 |

(Continued)

*Primary Examiner* — Deanna K Hall
(74) *Attorney, Agent, or Firm* — Levine Bagade Han LLP

(57) ABSTRACT

Devices, systems, and methods for treating chronic rhinosinutisits (CRS) are described herein. The devices can have a guide member defining at least one lumen therethrough. A drug delivery component is advanced through the lumen to deliver a substance to the sino-nasal cavity of a patient. Once the drug delivery component is positioned at the desired area in the sino-nasal cavity, a user actuates the system to deliver the substance to the target area. Actuation of the system delivers the substance to the middle meatus, osteo-meatal complex, or other areas within the sino-nasal cavity of the patient.

13 Claims, 22 Drawing Sheets

(56) References Cited

U.S. PATENT DOCUMENTS

| | | | |
|---|---|---|---|
| 2013/0245609 A1* | 9/2013 | Schaeffer | A61M 31/00 604/218 |
| 2015/0290439 A1 | 10/2015 | Eldrege et al. | |
| 2016/0002206 A1 | 1/2016 | Brotherton-Pleiss et al. | |
| 2016/0199599 A1 | 7/2016 | Isaacs et al. | |
| 2017/0128696 A1 | 5/2017 | Linden et al. | |
| 2018/0217145 A1 | 8/2018 | Skraba et al. | |
| 2018/0280606 A1 | 10/2018 | Wu et al. | |
| 2020/0338287 A1* | 10/2020 | Chan | A61M 15/0086 |

FOREIGN PATENT DOCUMENTS

| | | |
|---|---|---|
| WO | WO 2013/119258 | 8/2013 |
| WO | WO 2020/197995 | 10/2020 |

* cited by examiner

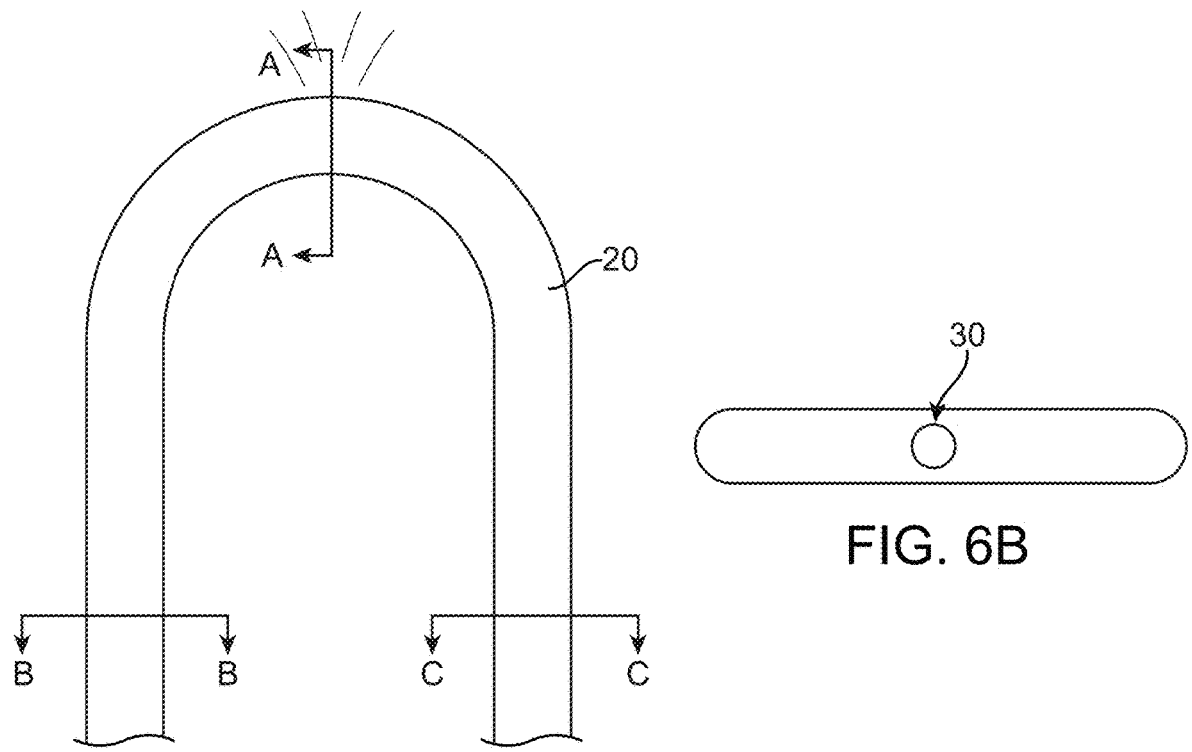
FIG. 6A
FIG. 6C
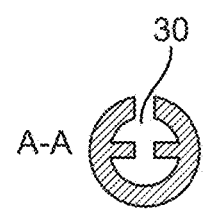
FIG. 6B
FIG. 6D
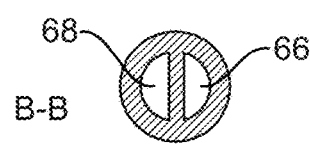
FIG. 6E
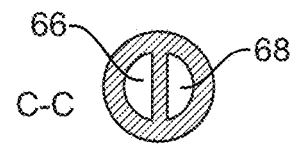
FIG. 6F

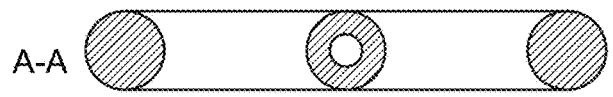
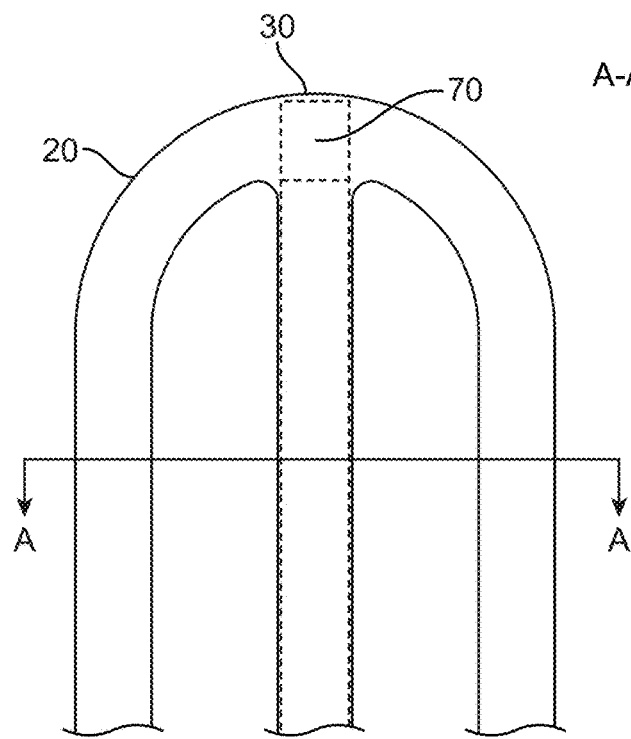
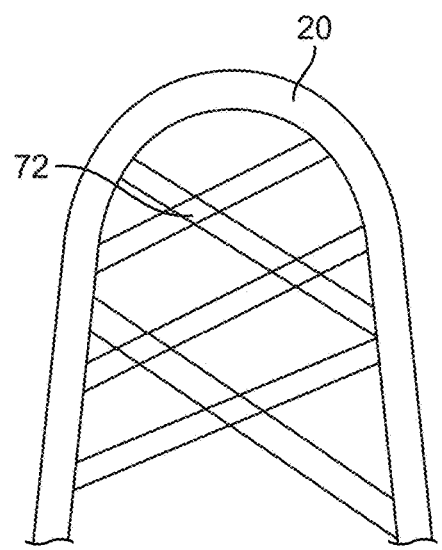
FIG. 7B
FIG. 7A
FIG. 8
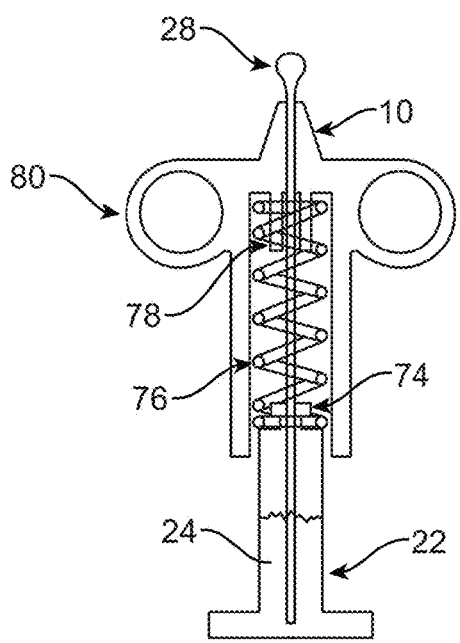
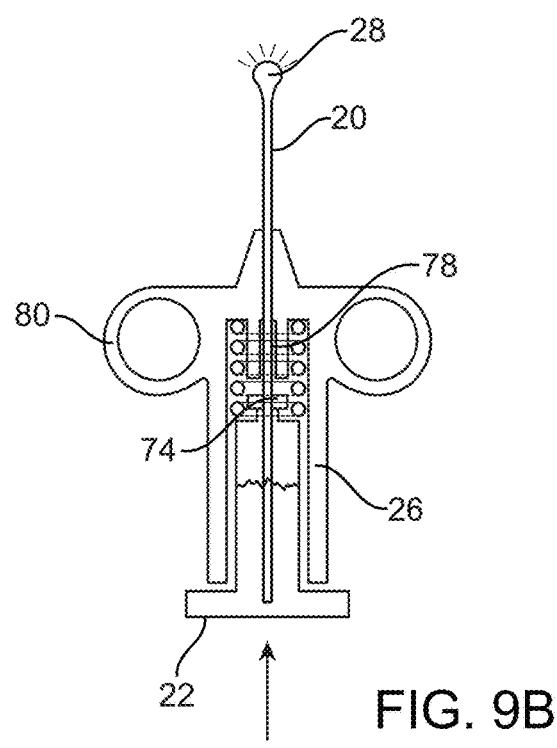
FIG. 9A
FIG. 9B

NASAL DRUG DELIVERY SYSTEM

CROSS-REFERENCE TO RELATED APPLICATIONS

This application is a continuation of International Patent Application No. PCT/US2020/023826 filed on Mar. 20, 2020, which claims the benefit of priority to U.S. Prov. Apps. 62/825,668 filed Mar. 28, 2019; 62/862,562 filed Jun. 17, 2019; and 62/915,371 filed Oct. 15, 2019, each of which is incorporated herein by reference in its entirety.

STATEMENT REGARDING FEDERALLY SPONSORED RESEARCH OR DEVELOPMENT

This invention was made with Government support under contract TR003142 awarded by the National Institutes of Health. The Government has certain rights in the invention.

FIELD OF THE INVENTION

This application relates generally to medical devices and methods. More particularly, the application relates to systems and methods for delivering medication to a patient's nasal cavity.

BACKGROUND OF THE INVENTION

Chronic rhinosinusitis (CRS) affects approximately 20 million patients in the United States each year. CRS results from a dysfunctional interplay between host characteristics and exogenous factors. Symptoms include nasal blockage/obstruction/congestion, nasal discharge, facial pain/pressure, and reduction of smell. These symptoms can significantly affect quality of life, sleep quality, and work productivity and can persist for more than 12 weeks.

Sinonasal anatomy is complex, composed of intricate and subdivided pathways that connect the sinuses in the nasal cavity. There are three turbinates within the nasal cavity and these turbinates are mucosal covered bony shelves increasing the interior surface area of the nasal cavity. Beneath each turbinate is a corresponding space called a meatus and there are four paired sinuses that are drained with the help of their corresponding meatuses. The osteomeatal complex (OMC) is the main gateway to sinus drainage. The OMC is a collection of structures including the middle meatus. Three of the four sinuses drain through the middle meatus. The OMC serves as the connection between the middle meatus and the frontal sinuses, uncinate process, anterior ethmoid, maxillary ostium, ethmoid infundibulum, and the anterior ethmoid cells, allowing for airflow and drainage.

Nasal anatomy can differ significantly across individuals. Variations in nasal anatomy can often lead to mechanical obstruction of the middle meatus and OMC leading to CRS. Such variations can include concha bullosa (aeration of the middle turbinate), nasal septal deviation (asymmetric bowing of the septum), and paradoxical middle turbinate (curvature of the middle turbinate), inferior turbinate hypertrophy, uncinate process medial rotation, agger nasi and hailer cells, among others.

Currently, treatment for CRS starts with medical therapy in the form of local medication administration. Sinonasal saline irrigations remove mucus and environmental triggers and assists in restoring normal mucociliary clearance. Saline irrigation is often improved when supplemented with steroid therapy. Topical steroids, typically administered with nasal spray, reduce sinonasal mucosal inflammation, decrease vascular permeability, and thin mucus by reducing glycoprotein release from submucosal glands. Additional topical medications include antihistamine, antichloingeric, antibiotic, and antifungal sprays, among others. Patients may be additionally treated with oral medications, namely systemic steroids and systemic antibiotics.

Other current methods of delivering topical medication to the middle meatus and OMC are done in the setting of a medical facility with direct endoscopic visualization. To be effective, however, medication must be delivered every day or every few days, which is impractical for most patients. Variation in individual patient nasal anatomy further complicates delivery.

Nasal steroid sprays are typically ineffective because they are unable to get past the most anterior portion of the nasal cavity, the nasal valve. If they do get past, they typically go to the back of the throat to the airway and swallow regions. The sprays have difficulty in reaching under the middle turbinate to the middle meatus, which is the basin where three of the four sinus cavities drain. In addition, it is a torturous pathway from the external nose to the middle meatus, and natural flow conditions do not carry sprays to the middle meatus region.

The inability to reach the middle meatus has been verified in the lab by loading standard nasal spray bottles with saline and blue dye. The liquid was sprayed in human subjects' noses and the nasal anatomy was inspected with endoscopic video with areas of deposition coated in blue. The results confirmed that a majority of the spray was deposited in the internal nasal valve, with very little to no spray being deposited in the middle meatus. The literature also confirms that 1-3% of the spray may reach the middle meatus, and this includes patients' spraying with specialized, twisted head maneuvers.

Many of the conventional methods are directed to deploying a spray between the interior and exterior nasal valve and using means such as breath power, e.g., as implemented by the Exhalation Delivery System by OptiNose US, Inc. (Yardley, PA), to disperse the droplets further back. However, when performed the same aforementioned lab test with saline and dye, it was confirmed that the saline still does not access the middle meatus in any significant quantity.

Typical guidelines state that the correct usage of nasal steroid sprays include the following:
  A. Look down at the floor so the spray is directed towards the nasal airway, to cover the inferior turbinate, and not to the blind pouch of the nasal valve.
  B. Aim nozzle to the lateral inner corner of the eye so that the spray does not bathe the septum.
  C. Sniff gently so the drug does not go too far back and into the vocal cords and lungs.

However, many patients buy products over-the-counter and do not read instructions on how to use them, many physicians do not spend the time counseling patients correctly, and even when the instructions are explained, many patients are non-compliant.

Thus, there is a need in the art for a device and method to easily, effectively, and non-invasively deliver local medical therapy to the target spot of the middle meatus and OMC of any patient as needed.

There is a further need for delivery of agents to the middle meatus and OMC without any need for special head positioning by the patient, thus eliminating the above problems and human factors.

SUMMARY OF THE INVENTION

This disclosure relates generally to the delivery of medical therapy to the OMC for treatment of various conditions including CRS using a nasal drug delivery system. Specifically, the nasal drug delivery system may have a guide member introduced into the nostril of a patient and the guide member may have a lumen therethrough. The system may have a container for carrying the substance within and a flexible member extending within the container and insertable through the lumen. The flexible member may have one or more openings near a distal end where the opening may be in fluid communication with the container. The system may have an actuator that, when triggered, delivers the substance through the one or more openings and to the nasal cavity, specifically within the middle meatus. The drug delivery component may be long enough to reach past the inferior turbinate and into the middle meatus of the nasal cavity and the drug delivery component may have a preset shape such as a curved portion, a loop, or a pigtail shape to facilitate entry and positioning into the middle meatus.

Experimentation with anatomic models and human testing revealed the following challenges and also illustrate how the present devices and methods disclosed herein may overcome these challenges.

Passing through the interior nasal valve, as described above, the interior nasal valve is an elongated, narrow passageway. Therefore, the delivery section of the device is ideally thin enough or flexible enough to compress while passing through this section, especially in patients with inflammation that further narrows the passageway.

In another variation, the nasal drug delivery system may have a guide member having a lumen therethrough and an alignment member extending at an angle from the guide member. The alignment member may be in contact with the patient when the guide member is inserted into the nasal cavity. The alignment member may optionally have an adjustable hinge to change the angle between the guide member and the alignment member. The system may further include a reservoir for carrying the substance within. The system may further include a flexible member extending within the reservoir. The flexible member may be inserted through the lumen of the guide member and the flexible member may be in the shape of a looped member. The flexible member may have one or more openings near a distal end where the openings may be formed in a nozzle configuration. The system may further include an inner member coupled to the flexible member and slidable while fluidly coupled to or optionally within the reservoir. Sliding the inner member within the reservoir may expose the flexible member to the nasal cavity and the inner member may have an actuator which, when triggered, delivers the substance through the one or more openings and to the nasal cavity.

Additionally, methods for treating CRS or other diseases by delivering a substance to a nasal cavity of subject are provided. The methods may include inserting a guide member into the nostril of a subject. A tube may be extended through a lumen of the guide member and the tube may have one or more openings in fluid communication with a container. The container may hold a substance to be delivered to the nasal cavity upon triggering of an actuator. The system may also atomize the drug to be delivered before it exits the tube.

The device shown and described herein may further include the following features and advantages.

An alignment guide may enable the patient to locate and position the device with respect to a relatively solid reference plane, for example, the maxilla, teeth and bone structure in front of and under the upper lip. This sets a constant introduction angle, as determined by assessing CT scans, creating 3D printed anatomic models, and human clinical trials.

The guide member may provide structure and sets the introduction angle in conjunction with the alignment guide up to the nasal valve. Without this rigid structure, the angle may not be set properly.

The loop configuration of the drug delivery component may be atraumatic because of the gentle curve.

The loop configuration of the drug delivery component may be atraumatic because there are no sharp edges.

Since the drug delivery component is composed of a flexible material and is in a loop configuration, it can compress, as described herein, when passing through the small opening of the inflamed nasal valve. If it were solid, yet still flexible, it may not be able to compress.

Since the loop configuration of the drug delivery component comprises two straight portions that are spaced far apart relative to their diameters, it maintains the introduction angle well as the component is advanced through the anatomy. Alternative designs may comprise single members.

The two straight portions of the drug delivery component are preferably rigid enough to push through the anatomy, including approximated, inflamed mucosa, yet flexible enough to buckle under excessive loads in the "X" direction (as shown and described herein below) in order to minimize the risk of trauma and discomfort.

The two straight portions of the drug delivery component may be rigid enough to push through the anatomy, maintain the introduction angle, yet flex in the "Y" and "Z" directions (as shown and described herein below) to conform to the anatomy and enhance comfort.

The loop portion of the drug delivery component may enable deep access to the middle meatus for multiple anatomic variations:

A. The drug delivery component can leverage the anatomy of the inferior turbinate to successfully glide over it and past the internal nasal valve, even if the inferior turbinate is enlarged or inflamed.

B. The drug delivery component can be advanced until it contacts the lateral wall or the roof of the middle meatus. Upon further advancement of the component, the curve and flexibility of the straight members may allow for the component to ride along this lateral or upper wall, while advancing farther back, as described herein. Furthermore, the gentle distal curve may guide the component to enter the proximal entry of the middle meatus cavity (anterior aspect of the middle turbinate) and follow the lateral or upper wall even if the introduction angle is not perfectly optimized for the patient's anatomy. This in effect accommodates anatomic variation.

As advanced, the angled distal portion of the drug delivery component may cause the device to preferentially enter the middle meatus (lateral), rather than the medial path of the nasal passage between the septum and the turbinates.

The angled portion of the drug delivery component may allow it to ride along the lateral inferior turbinate, rather than the medial septum. Since the septum is significantly more sensitive, this minimizes discomfort upon device insertion and removal.

The angled portion of the drug delivery component may cause the spray to be aimed lateral, rather than medial. This helps to avoid spray deposition on the septum which can cause mucosal thinning on the more delicate septum and bleeding.

The rotation of the loop, e.g., 180 degrees or 360 degrees, may allow the patient to use the same device in either nostril.

Since the spray can be deployed at any time, the user can determine the end of travel, thus accommodating various anatomies, including a more shallow nose, levels of patient tolerability, and disease states (e.g., severity of inflammation).

An indicator may be used to show the patient which side the device is set for.

Mucus traps molecules and delivers them to the throat where they are blown out of the nostrils or swallowed into the gastrointestinal tract. Therefore, drugs pass through this mucus layer to reach the surface of the mucosal lining, the epithelium, in order to be well absorbed. The drug delivery component may create a mechanical wiping action of the nasal passage during insertion and removal. This may be advantageous in clearing mucus for better drug absorption.

In a clinical trial study of 16 patients with CRS, the device successfully accessed the middle meatus in 94% of nostrils. This was with patient blind self-insertion, and physician endoscopic confirmation after placement.

In order to administer targeted therapy to the middle meatus anatomy, this would typically have to be done by a physician with instrumentation and direct visualization (e.g., endoscopy) in the office or operating room setting. The device described herein allows the patient to access this anatomy and self-administer targeted therapy in the home setting, without the physician, instrumentation, and direct visualization.

An atomization component may be incorporated into the looped portion. The embedding of a swirl atomizer into a flexible catheter may have applications beyond the present device.

BRIEF DESCRIPTION OF THE DRAWINGS

FIGS. 6A to 6F show top and cross-sectional views of a variation of the system of FIG. 3A with the loop having multiple lumens.

FIGS. 7A and 7B show top and cross-sectional views of a variation of the system of FIG. 3A with the loop having a center tube.

FIG. 8 shows a side view of a variation of the system of FIG. 3A with the loop having support members.

FIGS. 9A and 9B show side views of yet another variation of a nasal drug delivery system having an integrated component.

DETAILED DESCRIPTION OF THE INVENTION

This disclosure relates generally to nasal drug delivery devices and procedures. Specifically, it relates to devices and methods for delivering medical treatment to the middle meatus and OMC. The devices and methods disclosed can apply medical treatment to any variations in nasal cavity structure (e.g., different curvatures within the cavity). Therefore, the devices may be used by any patient regardless of anatomy.

Since the anatomy of the nasal cavity does not typically allow for easy access to these areas, the devices herein may generally involve advancing a drug delivery component directly to the target areas for easier delivery of the drug proximal, into and past the nasal valve and into and past the middle meatus. Other variations may incorporate features in combination for delivering drugs in other regions of the nasal cavity such as the nasal valve and/or inferior turbinate regions which are typically covered by conventional nasal spray devices. The devices and methods may then deliver the treatment directly to those specific areas in order to treat CRS and other diseases. The devices and methods may be used by the patient themselves, or with the assistance of a medical professional.

Figure 1B:
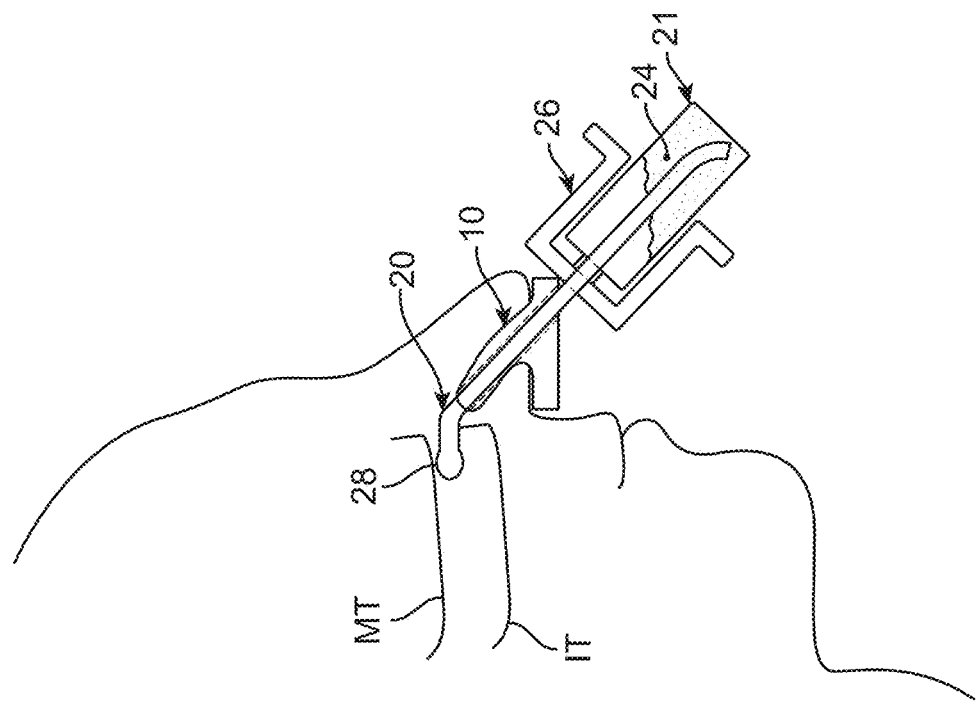
FIGS. 1A to 1E show side views of one variation of the nasal drug delivery system.
Figure 1A:
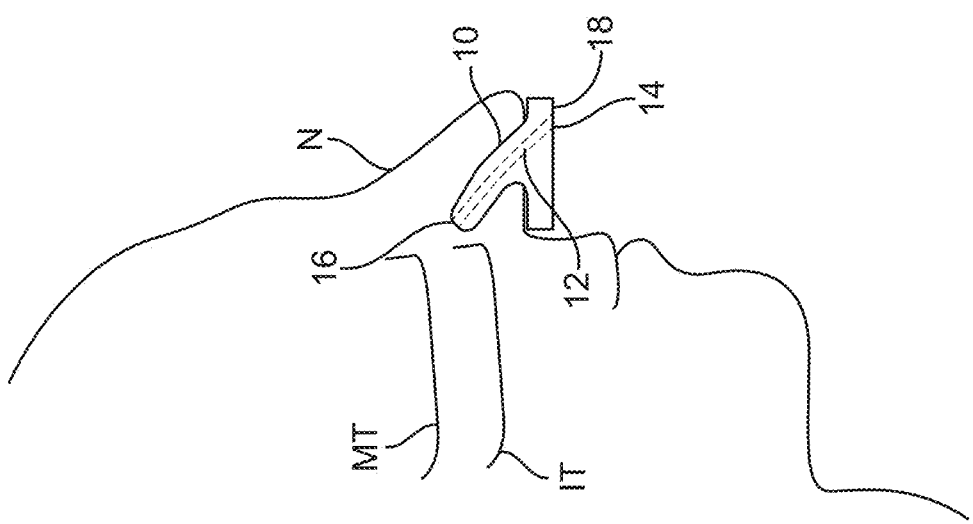

Referring to FIG. 1A, one example of the guide member 10 is shown in use for insertion into the nose N of the patient. The guide member 10 may be generally cone-shaped and may have a flared or expanded base 18 that rests against the opening of the nostril of the nose N of the patient so that the patient's nostril may be used as an anchor to position the guide member 10 within the nostril. The guide member 10 may also be shaped to use the nasal spine, lower lip, outside of nose, face, or teeth as an anchor for positioning. The guide member 10 may have a guide channel 12 to direct the drug delivery component 20 within the nasal cavity. A proximal opening 14 and a distal opening 16 define the guide channel 12. Although shown in FIG. 1A as a single guide member, it may have one or two prongs and inserted into one or both nostrils simultaneously. The length of the guide member 10 may range from, e.g., about 0.1 inches to 3 inches. In embodiments in which the guide member 10 is inserted into both nostrils, the guide member 10 comprises multiple guide channels 12 to direct the drug delivery device.

The guide member 10 may be constructed from a variety of materials including, but not limited to, silicone, plastic, polycarbonate, thermoplastic elastomer (e.g., between 30 and 80 Shore A), metal, or any other synthetic material. Specifically, materials such as elastomer at the proximal and distal openings may slightly compress against the drug delivery component 20 for a tight or secure fit as desired. A sponge or other material containing an antiseptic (e.g., alcohol) may be located within the guide member 10 and in contact with the drug delivery component 20 for the purposes of cleaning the drug delivery member when it is translated.

The geometry of the guide member 10 may be such that it directs the subsequently inserted drug delivery component 20 past the inferior turbinate IT and towards the target anatomy. The geometry of the guide may be determined by one or a combination of following measurement processes: 1) extrapolation from an individual's imaging data (including CT, MRI, ultrasound, optical methods, and x-ray radiographs); 2) custom molding; or 3) predetermined shapes and sizes, each of which is described in further detail herein.

Figure 1C:
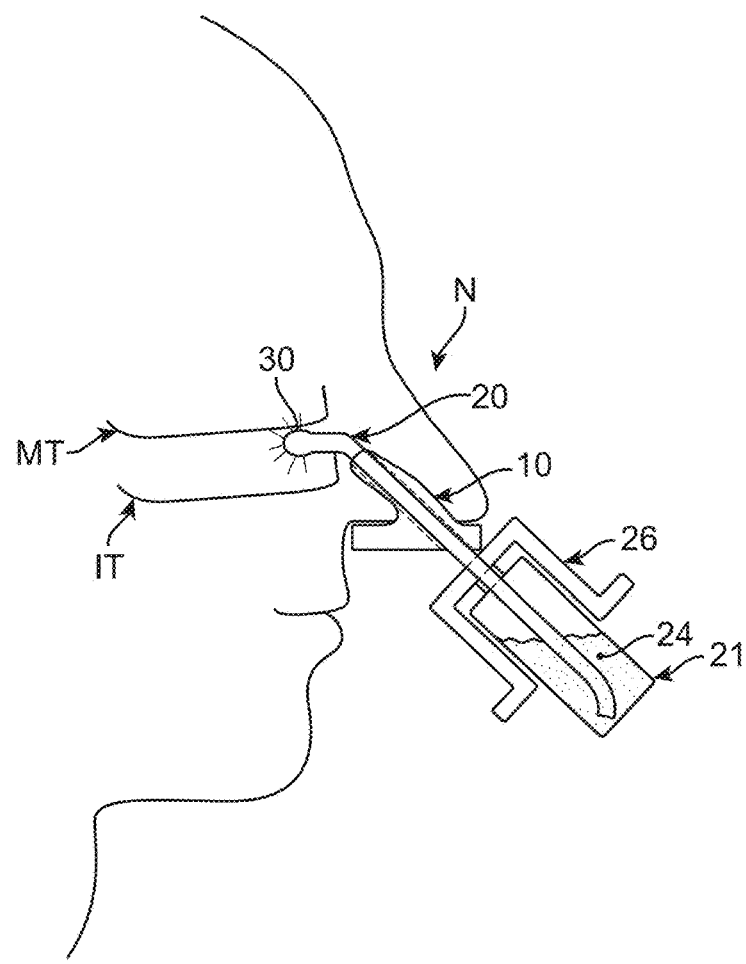
Figure 1D:
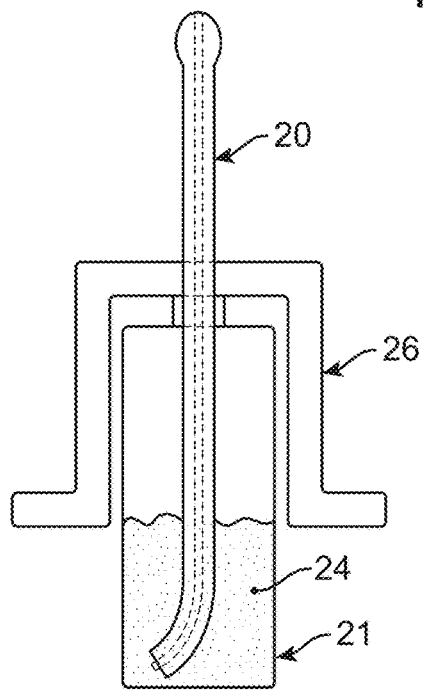
Figure 1E:
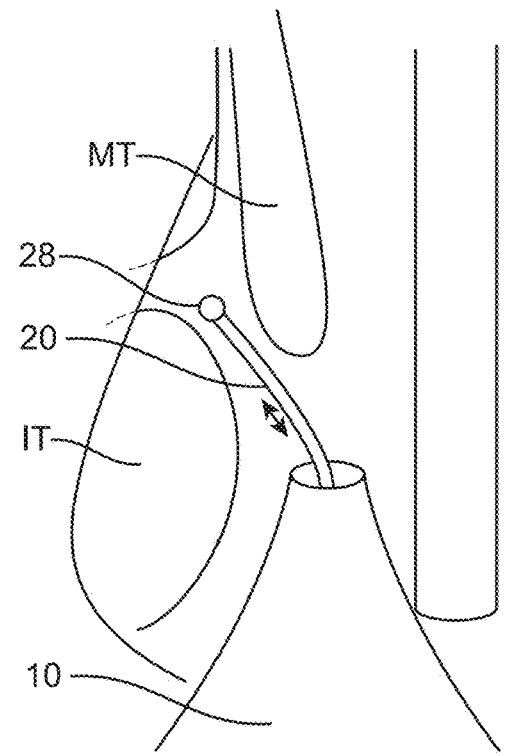

Once the guide member 10 is inserted into the nose, the drug delivery component 20 may be inserted in the proximal opening 14 of the guide member 10 and through the guide channel 12, as shown in FIG. 1B. The drug delivery component 20 may generally comprise an elongate structure with openings at both a proximal and/or a distal end. The drug delivery component 20 may be a solid but flexible member. The drug delivery component 20 may include a bulbous tip 28 at the distal end in part to present an atraumatic surface to the tissues as the tip 28 is inserted or removed. The drug delivery component 20 may be of a length such that the distal end reaches past the inferior turbinate IT and to the middle turbinate MT or further into nasal cavity, and more particularly to the middle meatus or OMC area, as shown in FIG. 1E. The drug delivery component 20 may ride along the inferior turbinate IT and insert itself within the middle meatus MM. The drug delivery component 20 may extend anywhere from, e.g., 0.1 to 2 inches, past the distal opening 16 of the guide member. The drug delivery component 20 may be relatively thin with a round or circular cross section to present an atraumatic surface to minimize discomfort to the patient.

The proximal end of the drug delivery component 20 may be carried by a drug container 21 which may or may not be attached to the guide member 10. The drug container 21 may take a cylindrical shape but may take any number of other shapes, e.g., such as a rectangular shape. The drug container 21 is in fluid communication with the drug delivery component 20, which may sit within drug container 21, as shown in FIG. 1D. The drug container 21 may carry any number of drugs or agents 24 for treatment of CRS or another disease state (e.g., saline, steroids, antihistamines, anticholinergics, antibiotics, antifungals, etc.). Triggering of an actuator 26 located between the guide member 10 and the drug container 21 may be used to deliver the drug 24 from the drug container 21 to the distal end of the drug delivery component 20, and eventually through one or more holes or openings 30, as shown in FIG. 1C, which may have a diameter of, e.g., around 0.01 inches. The openings may be in the form of an atomizer to create an aerosol. The actuator 26 may be a spring mechanism as shown, for example, in FIGS. 9A and 9B described below. However, it should be understood, that the drug may be ejected from the container in any suitable way, including, but not limited to automated or manually actuated pumping mechanisms, e.g., a manual squeezing mechanism, a pressurized cartridge, a spring-wound pump, or the like.

The drug or agent 24 may be for local and/or systemic treatment and may include, but are not limited to crystalloids, corticosteroids, antihistamines, anticholinergics, antibiotics, antifungals, triptans, metabolites, NSAIDs, hormones, central nervous system agents, benzodiazepines, or anesthetics. The drug or agent may be also be sterile water, saline, a decongestant, cromoglycates, mucolytics, analgesics, antiemetics, insulin, hormones, antimigrane medications, antiepileptics, sedatives, hypnotics, cardiovascular drugs, proteins, peptides, vaccines, or a combination thereof, etc. The drug 24 may also be thixotropic or embedded in a thermosenstive gel or in a foam. The drug 24 may also optionally have mucoadhesive properties to increase residence time The system may optionally include an antiseptic contained in a case 51 that contacts the drug delivery component 20 and the guide member 10 or a reservoir in which the drug delivery component 20 and the guide member 10 is stored to maintain cleanliness between uses, as shown in FIGS. 3O and 3P. The device may also be stored inside a storage container 51 having a light 55 or emitter that emits light 57 in the UV spectrum to sterilize the guide member 10, drug delivery component 20, and other portions of the device contained within the compartment 53. The UV light may also be optionally embedded within the device and can be activated to sterilize the device when the device is not in use.

Figure 2A:
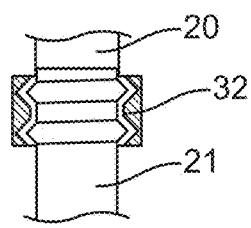
FIGS. 2A and 2B show side views of connections between the drug delivery component and the drug container.
Figure 2B:
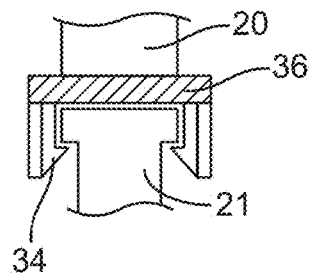

The drug delivery component 20 and the drug container 21 may also be connected by an attachment that prevents leakage. Referring to FIG. 2A, the drug container 21 and the drug delivery component 20 may be connected by any number of releasable securement mechanisms, e.g., a threaded or screw-top engagement 32. Alternatively, the drug container 21 and the drug delivery component 20 may be connected by, e.g., a snap-fit 34, as shown in FIG. 2B. A washer 36 may be placed on the snap-fit 34 to further seal the connection. It is to be understood that a custom attachment may also be used to connect the drug container 21 and the drug delivery component 20.

Figure 3A:
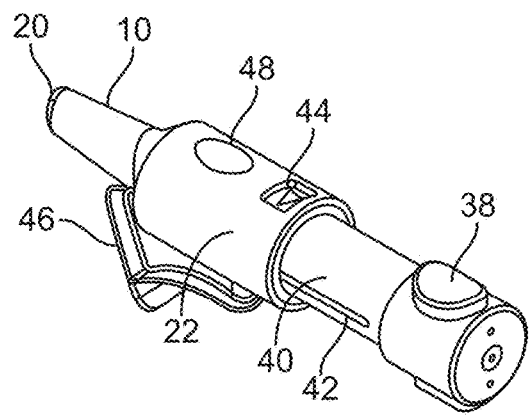
FIGS. 3A to 3D show perspective and side views of another variation of a nasal drug delivery system having an alignment guide and a loop.
Figure 3B:
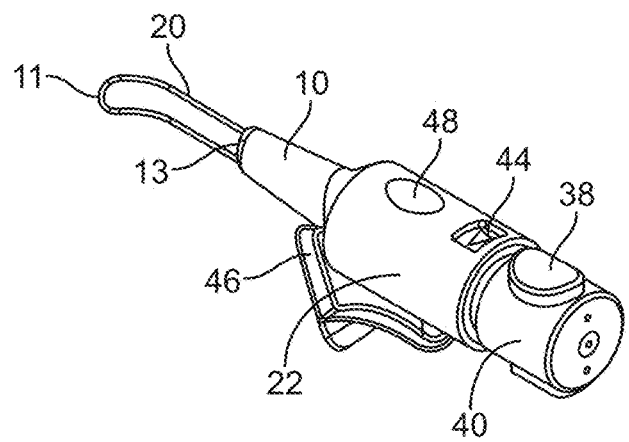
Figure 3C:
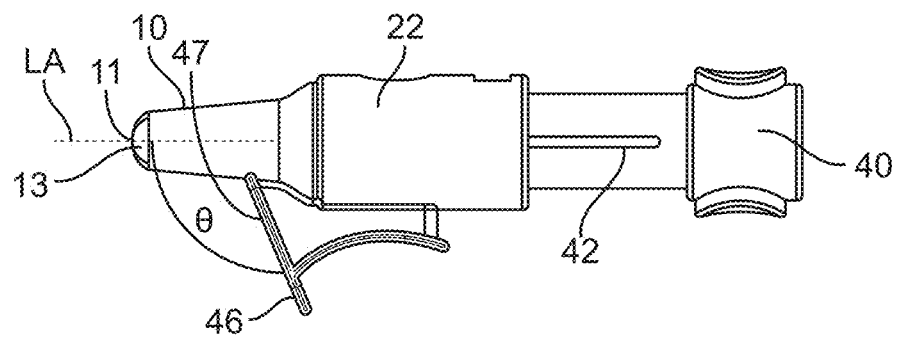
Figure 3D:
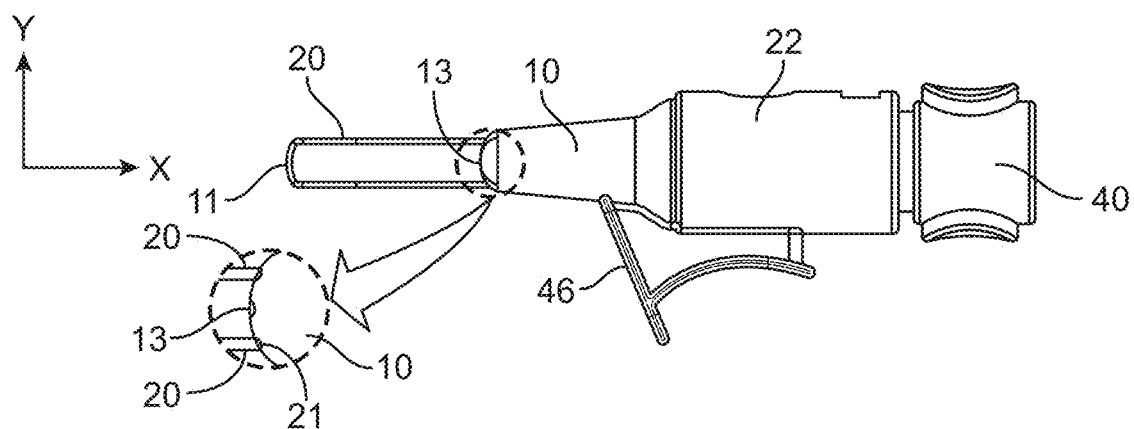
Figure 3E:
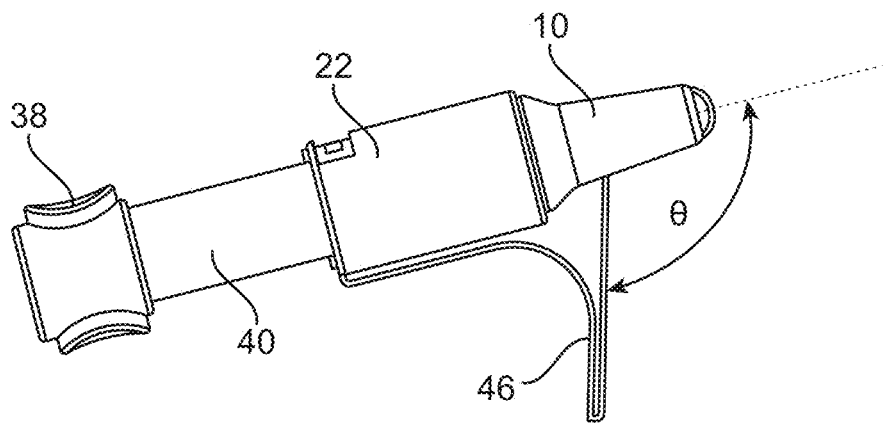
FIGS. 3E to 3G show additional side and perspective views of the system of FIG. 3A with the alignment guide adjusted at an angle relative to the longitudinal axis of the guide member.
Figure 3F:
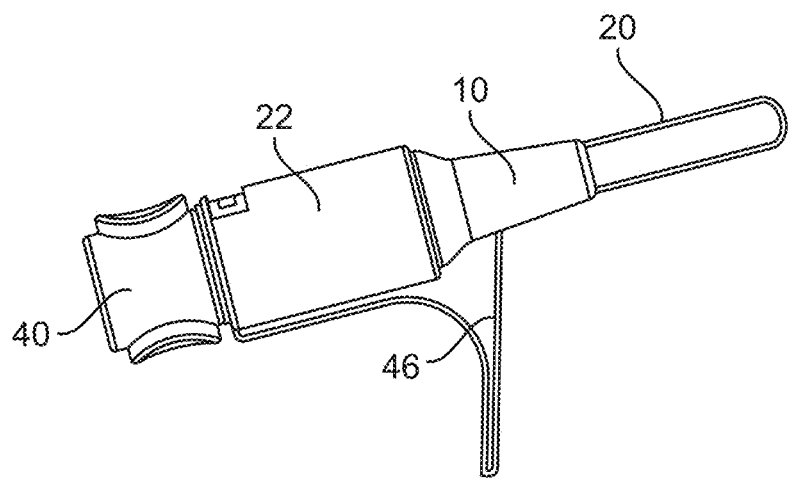
Figure 3G:
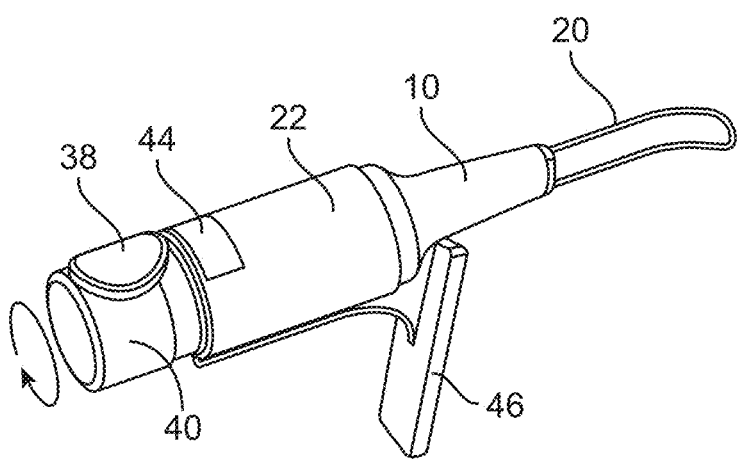
Figure 3H:
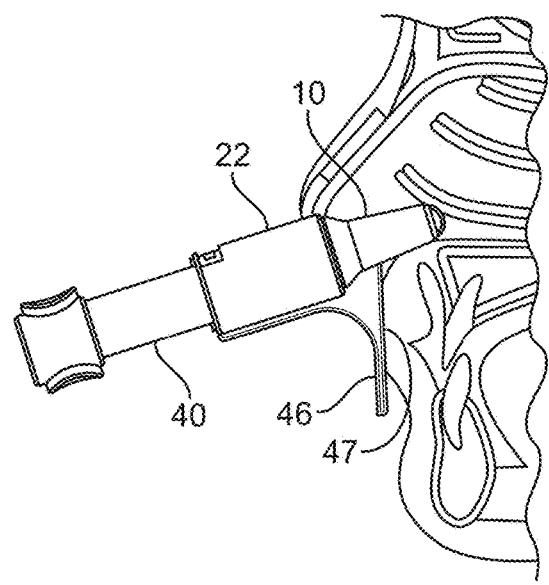
FIGS. 3H to 3J show side and front views of the system of FIG. 3A being delivered to the middle meatus of a subject.
Figure 3I:
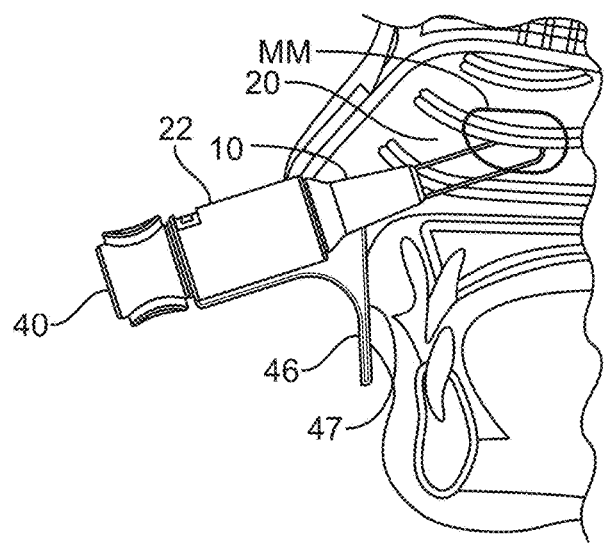
Figure 3J:
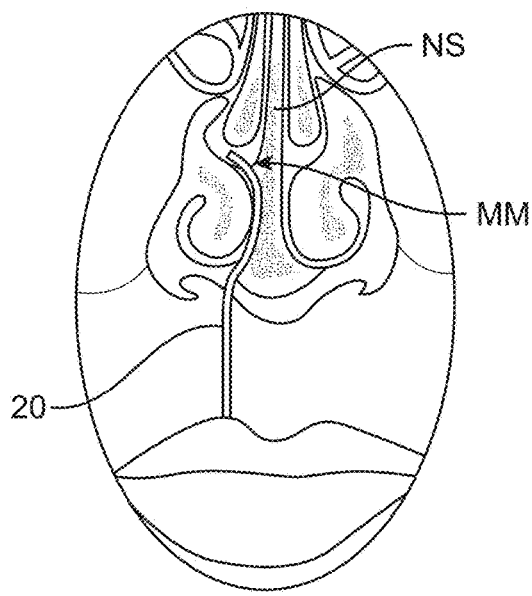
Figure 3K:
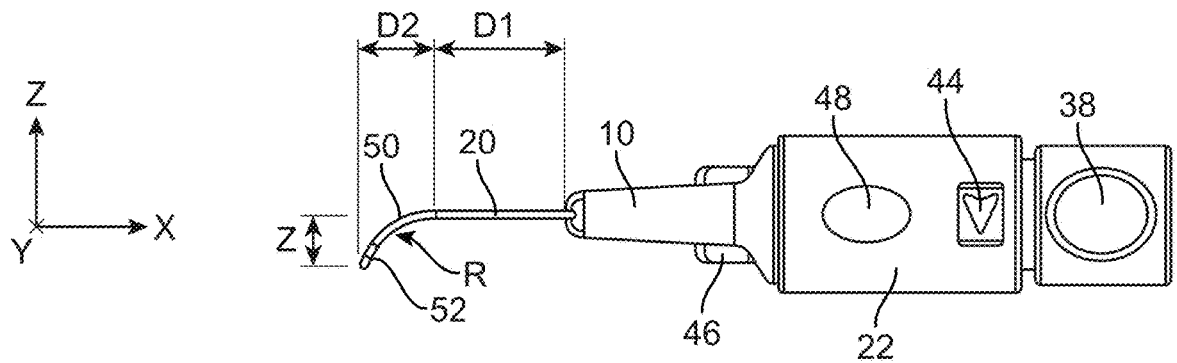
FIGS. 3K to 3N show top views of the system of FIG. 3A with the loop being rotated in different directions.
Figure 3L:
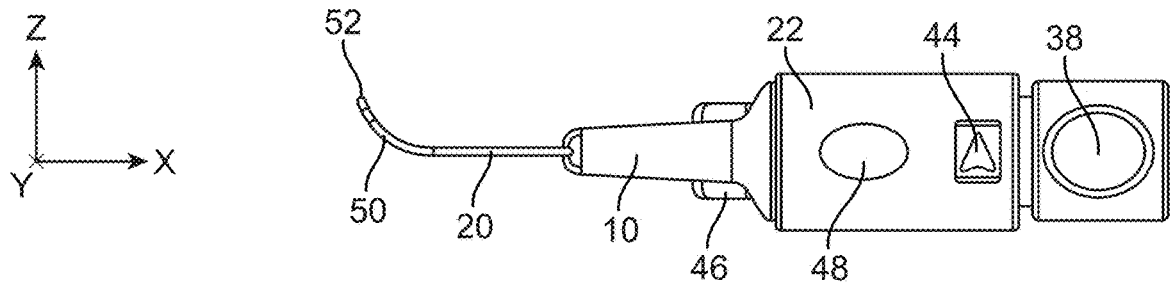
Figure 3M:
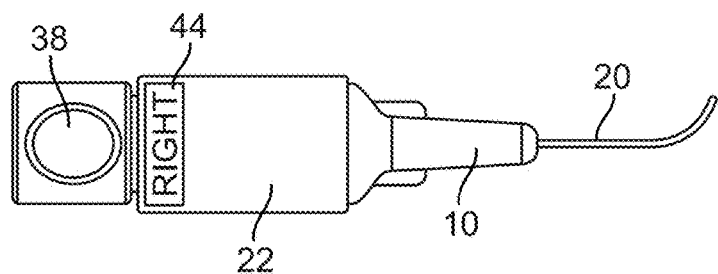
Figure 3N:
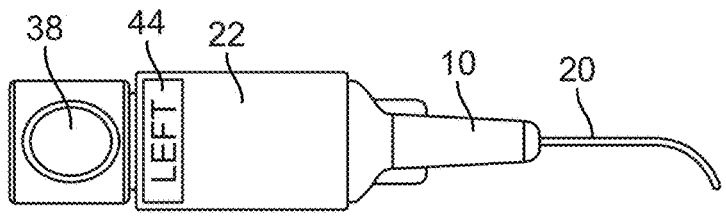
Figure 3O:
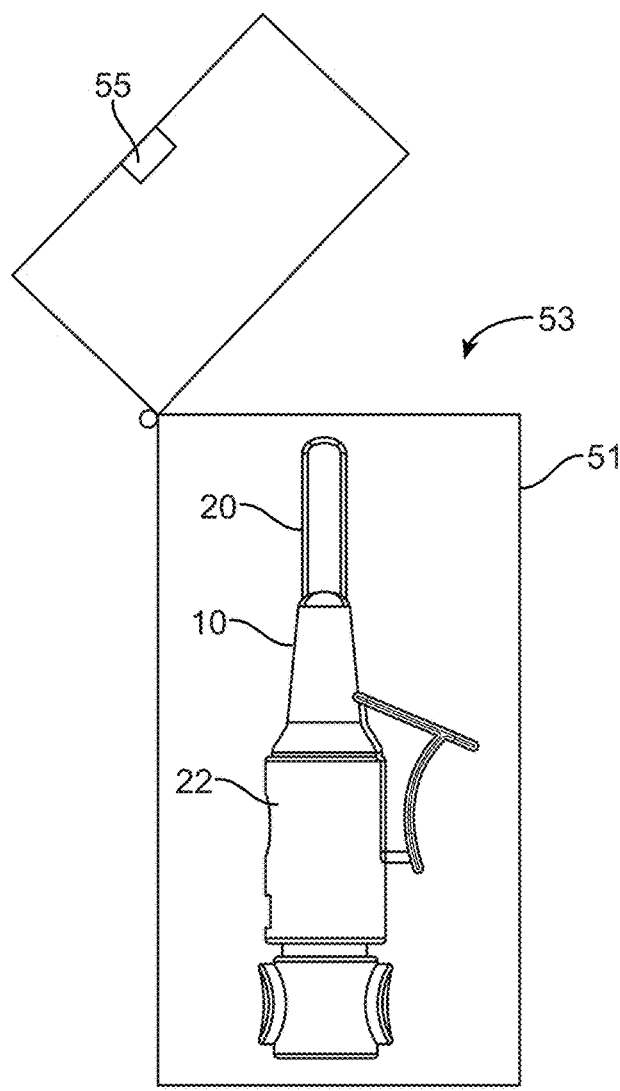
FIGS. 3O and 3P show side views of one variation of a case for storing the device and sterilizing between uses.
Figure 3P:
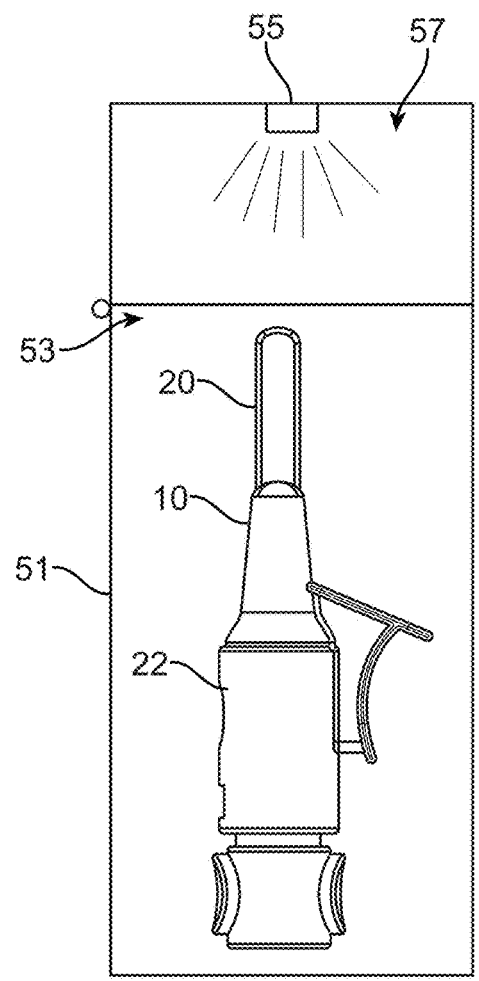

FIGS. 3A to 3N show another variation of the nasal drug delivery system. In this embodiment, a sliding member 40 may be used to advance and retract the drug delivery component 20. The sliding member 40 may be positioned within a guide housing 22 and may translate distally and proximally with respect to the guide housing 22 via slot 42. The sliding member 40 is connected to the drug delivery component 20, which may be configured to have two arm members extending in parallel and forming a flexible loop joined at the distal end of the component 20, as shown in FIG. 3B.

The loop configuration of the drug delivery component may be atraumatic because of the gentle curve and because there are no sharp edges. Since the drug delivery component is composed of a flexible material and is in a loop configuration, it can compress, as described herein, when passing through the small opening of the inflamed nasal valve. If it were solid, yet still flexible, it may not be able to compress.

Since the loop configuration of the drug delivery component comprises two straight portions that are spaced far apart relative to their diameters, it maintains the introduction angle well as the component is advanced through the anatomy. Alternative designs may comprise single members.

The two straight portions of the drug delivery component are preferably rigid enough to push through the anatomy, including approximated, inflamed mucosa, yet flexible enough to buckle under excessive loads in the "X" direction (as shown and described herein and with reference to FIGS. 3I, 3R, and 3K-3L) in order to minimize the risk of trauma and discomfort.

The two straight portions of the drug delivery component may be rigid enough to push through the anatomy, maintain the introduction angle, yet flex in the "Y" and "Z" directions (as shown and described herein and with reference to FIGS. 3I-3L and 3Q-3R) to conform to the anatomy and enhance comfort.

The loop portion of the drug delivery component may enable deep access to the middle meatus for multiple anatomic variations:

A. The drug delivery component can leverage the anatomy of the inferior turbinate to successfully glide over it and past the internal nasal valve, even if the inferior turbinate is enlarged or inflamed.

B. The drug delivery component can be advanced until it contacts the lateral wall or the roof of the middle meatus. Upon further advancement of the component, the curve and flexibility of the straight members may allow for the component to ride along this lateral or upper wall, while advancing farther back, as shown and described herein and with reference to FIGS. 3H-3J.

When advanced, the flexible loop may extend through the distal openings 16 in the guide member 10 and into fluid communication with a reservoir which may be contained within the sliding member 40, guide housing 22, or otherwise fluidly coupled to a reservoir in fluid communication in order to deliver the drug 24 through one or more openings 11 defined near or at the distal end of the component 20 and to the target area. The one or more openings 11 may have a diameter of around, e.g., 0.010 inches, although other diameters may be utilized, as described in further detail herein. Hence, the drug delivery component 20 may define a fluid lumen throughout the length of the flexible loop for introducing the drug for delivery to the patient. Additionally and/or optionally, the guide member 10 may also define or have one or more openings 13 near or at a distal end of the guide member 10 for dispersion of the drug as well. These openings 13 may be located, for instance, between the openings 21 through which the arm members of the drug delivery component 20 extend, as shown in the detail illustrated in FIG. 3D. In this manner, the drug may be dispersed from the one or more openings 11 at the end of the flexible loop simultaneously as the drug is dispersed from the one or more openings 13 at the end of the guide member 10 in order to disperse the drug throughout the nasal cavity. A user may advance the sliding member 40 within the guide housing 22 to this advanced position, as best shown in FIG. 3B. The guide housing 22 may have a finger indent 48 or another feature to accommodate the user's finger when holding the device for use. The loop may twist or bend 50 from a planar configuration when contained within the guide member 10 such that as the component 20 is advanced distally to exit from the constraints of the guide member 10, a distal portion of the component 20 may curve into a predetermined arcuate configuration relative to the proximal portion of the component 20. The distal curvature of the component 20 may be optimized to preferentially extend into the meatus between the turbinate tissues, as described in greater detail herein. A user may return the sliding member 40 proximally to its original position, retracting the flexible loop within the guide member 10, as shown in FIG. 3A. The loop and the guide member 10 may be easily removed from the guide housing 22 and the sliding member 40 so as to avoid contamination between uses. If necessary, the drug delivery component 20 may be inserted into the nose N without the use of the guide member 10.

An alignment guide may enable the patient to locate and position the device with respect to a relatively solid reference plane, for example, the maxilla, teeth and bone structure in front of and under the upper lip. This sets a constant introduction angle, as determined by assessing CT scans, creating 3D printed anatomic models, and human clinical trials. The guide member may provide structure and sets the introduction angle in conjunction with the alignment guide up to the nasal valve. Without this rigid structure, the angle may not be set properly. The alignment guide 46 is provided to facilitate positioning of the guide member 10 with respect to the patient's anatomy to guide the delivery component 20 into and through the nostril of the patient at an angle optimal for ensuring that the trajectory of the delivery component 20 during advancement into the nasal cavity tracks directly into the meatus, as described in detail below. The alignment guide 46 may be securely connected or otherwise integrated with the guide housing 22 to form a rigid structure where the alignment guide 46 may extend from the guide housing 22 at an introduction angle θ which may be defined between a contact surface 47 of the alignment guide 46 with respect to a longitudinal axis LA defined by the guide member 10, as best shown in FIG. 3C. The introduction angle θ may be set, e.g., at 112.5 degrees, but may range anywhere between, e.g., 110 to 120 degrees, and can be adjusted outside of that range if necessary. The alignment guide 46 can optionally incorporate a hinge in order to adjust the introduction angle θ as desired by the user. The alignment guide 46 in one variation may be configured as a flat plate as shown in FIGS. 3C and 3D or may be curved to allow the user to adjust the introduction angle to be angled more medial or lateral. The proximal end of the alignment guide 46 may be curved so as to accommodate the user's finger, as shown in FIG. 3C and alternatively in FIGS. 3E to 3G.

As shown in FIGS. 3H and 3I, the contact surface 47 of the alignment guide 46 may be brought into contact against the upper lip of the patient as the guide member 10 is inserted into the nostril. Alternatively, the guide member 10 may be positioned using a bite plate inserted into the patient's mouth. The guide member 10 may also be provided with a stop member that contacts the patient's nose N in order to prevent the guide member 10 from being placed too far distally inside the nostril. With the guide housing 22 and alignment guide 46 so positioned, the sliding member 40 may be advanced relative to the guide housing 22 to advance the looped delivery component 20 distally relative to the guide member 10 so that the looped delivery component 20 may slide or track against the tissue surface for positioning within the meatus. Because the looped delivery component 20 has a preferentially curved portion, the appropriate direction of curvature for the component 20 may be selected prior to advancing the device within the nostril depending upon which portion of the nasal cavity is being treated. For instance, if the device were used to treat the patient's right nasal cavity, the curvature of the looped delivery component 20 may be selected to extend in a first direction corresponding to the patient's right nasal cavity. In this manner, as the looped delivery component 20 is advanced within the patient's right nostril, the looped portion may extend from the nasal guide 10 so that the looped portion extends away from the patient's nasal septum NS and directly into the middle meatus MM, as shown in FIG. 3J which illustrates the looped portion seated within the right middle meatus MM of the patient after delivery.

Figure 3Q:
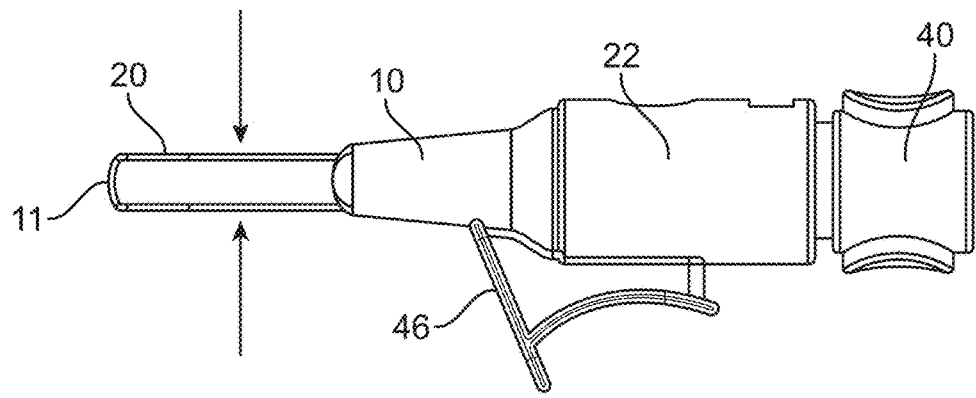
FIGS. 3Q and 3R show examples of how the delivery component may compress and flex for delivery into the nasal cavity.
Figure 3R:
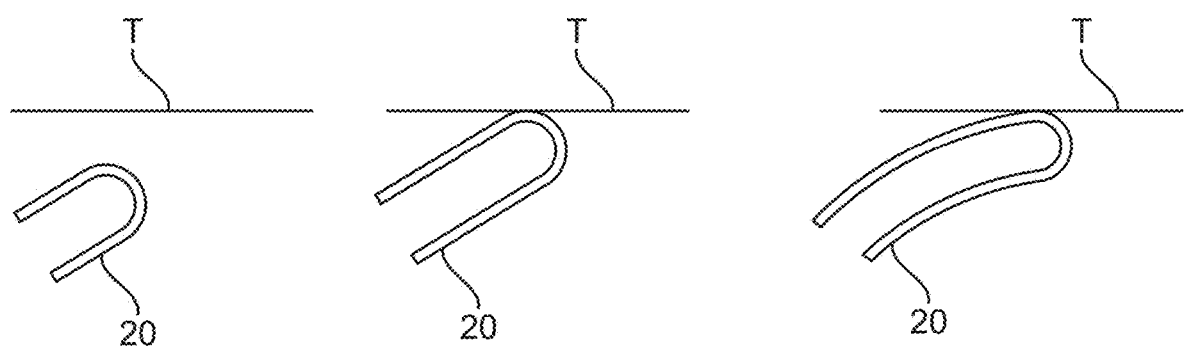

The design of the delivery component 20 may further allow for the arm members to be compressed, e.g., towards one another as shown in FIG. 3Q, as the device is advanced past tissue. This ability of the component 20 to compress without buckling may enable the device to be advanced past inflamed tissue or past anatomical protuberances. Additionally, the delivery component 20 may still retain its flexibility, as illustrated by the device shown in FIG. 3R being advanced into contact against a tissue region T and curving gently as it rides along the surface of the tissue, e.g. superior wall of middle meatus, during positioning and/or retraction.

As the pre-bent curved portion 50 is configured to readily seat itself in the middle meatus MM before delivery of the drug, the curved portion 50 may have a length D2 of about, e.g., 0.3 to 0.6 inches, which extends from a proximal portion of the drug delivery component 20 having a length D1 of about, e.g., 0.6 to 1.0 inches. The curved portion 50 may also have a radius of curvature R range from about, e.g., 0.3 to 0.6 inches, such that the terminal end of the curved portion 50 extends a distance Z of about, e.g., 0.2 to 0.5 inches, from a plane of the delivery component 20.

In another alternative variation, rather than having the curved portion 50 extending a distance, the distal portion of the delivery component may remain in a straightened configuration. One or more pull wires may be coupled along a length of the distal portion such that actuation of the pull wire relative to the delivery component may steer the distal portion into its curved configuration. Depending on the number of pull wires used or the attachment locations, the delivery component may be articulated into any number of configurations, as desired.

As best shown in FIGS. 3K to 3N, the user may rotate the sliding member 40 to change the direction of the looped portion 50 relative to the alignment guide 46 and guide housing 22 depending upon which portion of the nasal cavity is being treated. For example, if treatment of the second nostril were desired or required, the sliding member 40 can be manually rotated about its longitudinal axis to rotate the loop and guide member 10, e.g., 180 degrees, relative to the guide housing 22 and alignment guide 46. Orientation indicators 44 may be located on the guide housing 22 to signal to the user in which direction the looped portion 50 is curved so that, in one variation, the indicator may point in the same direction as the curvature of the looped portion 50. Orientation indicators 44 may be configured as arrows, as seen in FIGS. 3K and 3L, while alternative orientation indicators 44 may be include wording such as "RIGHT" or "LEFT", as shown in FIGS. 3M and 3N.

Optionally, the rotational motion used to change the positioning of the looped portion 50 relative to the guide housing 22 may be used to power or store up rotational energy for actuating the substance for delivery into the subject. For example, a rotational spring may be incorporated and wound as the device is rotated, as illustrated in the perspective view of FIG. 3G. This stored energy may then be used to impart an impulse to the substance contained within for ejecting the substance into the patient.

In some variations, the drug delivery component 20 may have portions which are configured to have differing stiffness levels. For instance, a dual hardness configuration may include the curved portion 50 having a hardness, e.g., 62 Shore D, which is relatively softer than the remainder of the delivery component in order to allow for the curved portion 50 to flex while passing through the interior nasal valve and other anatomy and ride along the tissue surface atraumatically while the proximal, stiffer portion of the component 20 may provide a hardness, e.g., 72 Shore D, having sufficient column strength to the component as the loop penetrates into the nasal cavity.

Once the drug delivery component 20 has been positioned near the target area of the nasal cavity, the user may press actuating buttons 38 to release the drug 24 out of the one or more holes or openings 30 defined along the curved portion 50 and into the target area. Additionally, the drug 24 may release into the nasal cavity through one or more distal openings 13 defined on the guide member 10 to allow for the drug 24 to reach an area that the drug delivery component 20 may not reach itself. In use, any combination of the openings may be utilized for drug release. For example, the one or more openings 30 along the curved portion 50 may be used alone or together simultaneously with the one or more distal openings 13 defined on the guide member 10. In other examples, the one or more distal openings 13 on the guide member 10 may be used alone. In yet other examples, any combination of openings along the delivery component 20 and/or guide member 10 may be used alone or together depending upon the desired treatment.

While a terminal end of the distal curved portion 50 of the drug delivery component 20 may define one or more openings for delivering the drug, the one or more openings may be configured in a number of different shapes. In its simplest variation, the openings may be defined as holes for passage of the drugs while in other variations, the one or more openings may be configured as nozzles for atomization.

Figure 4A:
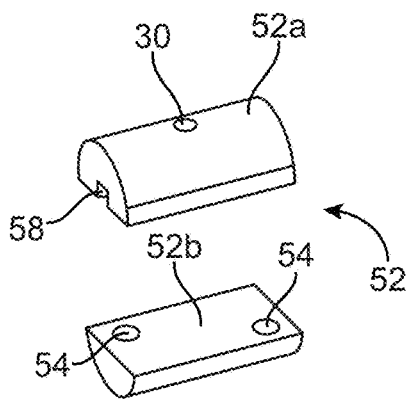
FIGS. 4A to 4J show various embodiments of a nozzle at the end of the loop of FIG. 3A.
Figure 4B:
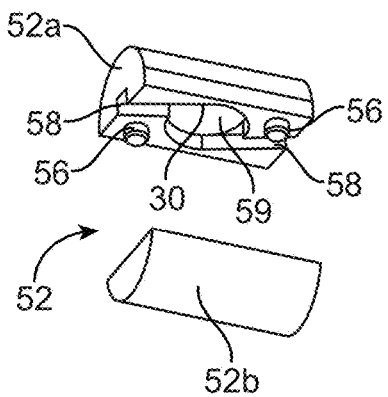

FIGS. 4A to 4J illustrate variations of a nozzle 52 at the distal end of the curved portion 50 of the drug delivery component 20 of FIG. 3A. While a single nozzle opening is illustrated, other variations may include multiple nozzles. The nozzle 52 may be comprised of two components 52a and 52b, as shown in FIGS. 4A and 4B, which may form a semi-circular shape. Nozzle component 52a may define two nozzle bores 58 at either side which are angled relative to one another. Nozzle component 52b may have nozzle holes 54 that receive pegs 56 protruding from the surface of nozzle component 52a for coupling and aligning the two components to one another although any number of securement mechanisms may be used.

Connection of the two components may form a spherical swirl chamber 59 into which the nozzle bores 58 may extend at an opposite tangential configuration such that when the drug or fluid is introduced through the two members of the drug delivery component 20, the drug or fluid may enter into the swirl chamber 59 tangentially from opposing sides so that the drug is swirled circumferentially within the chamber prior to exiting towards the one or more openings 30 and into the patient. In this manner, the swirl chamber 59 may help to atomize the drug 24 as it is ejected out of the one or more openings 30 to optimize its delivery onto the surrounding tissues. The nozzle components may be made of any number of materials such as polycarbonate, or any like material. Alternatively, the nozzle 52 may also be made of a single component instead of several. The nozzle 52 may be attached to the drug delivery component 20 or integrated to be part of the drug delivery component 20.

Figure 4C:
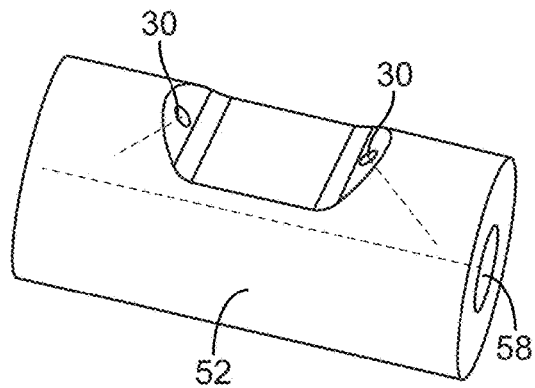
Figure 4D:
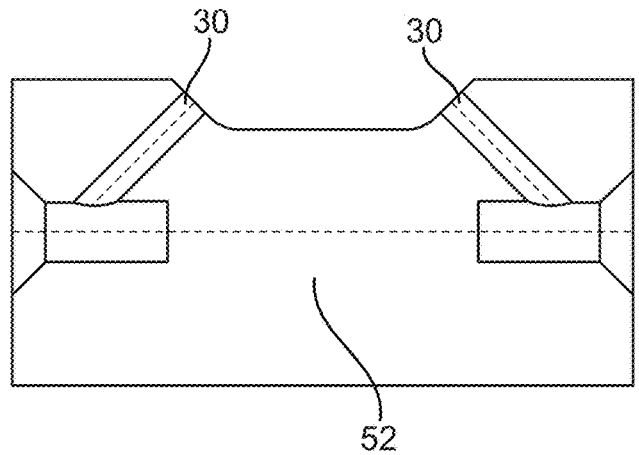

FIGS. 4C and 4D show another variation of the nozzle 52 at the distal end of the curved portion 50 of the drug delivery component 20 of FIG. 3A. In this example, nozzle 52 may be configured as an impinging jet having two openings 30, though any number of openings may be used. The openings 30 may have a diameter of, e.g., around 100 μm, and the nozzle 52 may be either moldable as two halves or made as an integrated component. The openings 30 may be angled from the longitudinal axis of the nozzle 52 such that the drug may exit out of the openings 30 at an angled trajectory and impinge upon one another to spread the spray pattern of the drug onto the tissue. The chamfer shape of the outside surface of the nozzle 52 may also allow for the openings 30 to be positioned at an angle with respect to the longitudinal axis of the nozzle 52.

Figure 4E:
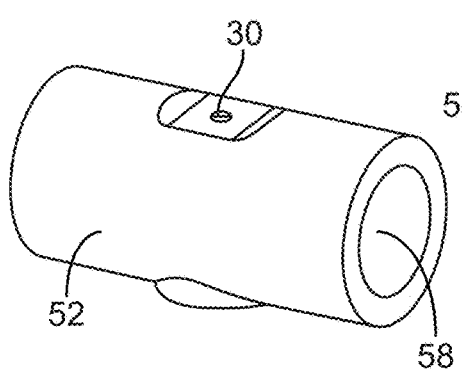
Figure 4F:
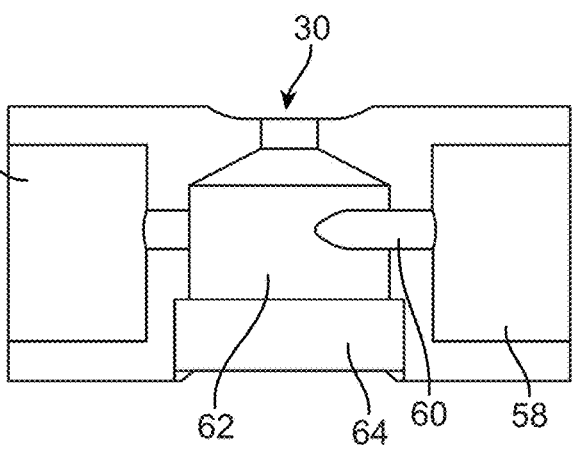

FIGS. 4E and 4F show yet another variation of the nozzle 52 including inlets 60 connected to a swirl chamber 62. The nozzle bores 58 carry the drug 24 from both members of the drug delivery component 20 to the swirl chamber 62 via inlets 60. The swirl chamber 62 may be structurally similar to the chamber 59 of FIGS. 4A and 4B but in this variation a plug 64 may be bonded to the swirl chamber 62 prevent any leakage of the drug 24 which may be delivered to the nasal cavity through one or more openings 30. The nozzle 52 may be micro-machinable where the bores and holes of the nozzle 52 may be created by drilling, milling, or any other suitable procedure.

Figure 4G:
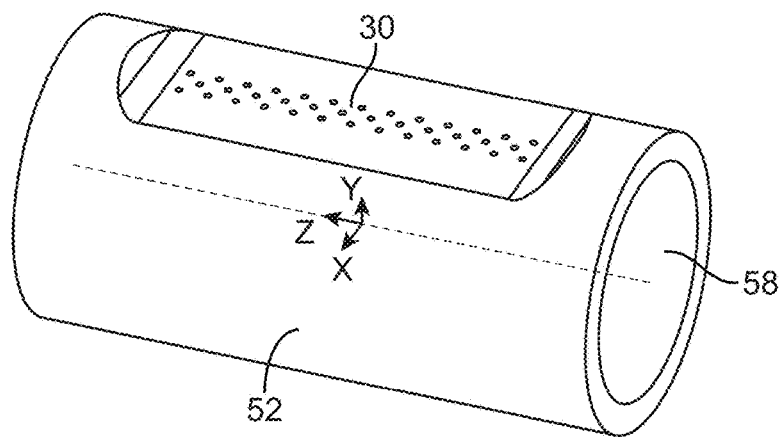
Figure 4H:
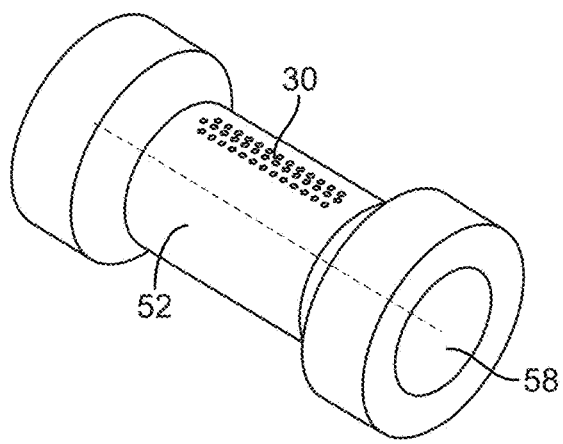
Figure 4I:
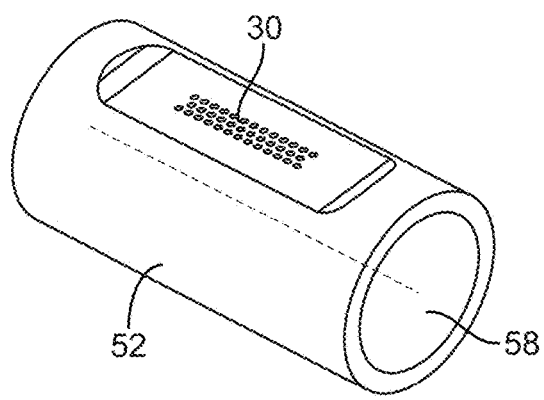
Figure 4J:
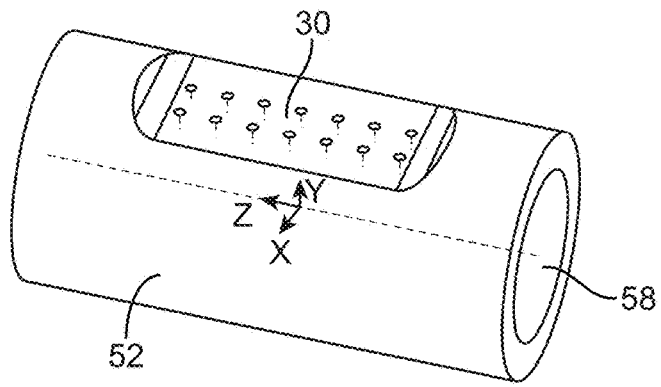

FIGS. 4G to 4J show further variations of the nozzle 52. As shown in FIG. 4G, the nozzle 52 may have several staggered rows of openings 30 for the drug to exit. The openings 30 may each be, e.g., about 20 μm, in diameter while defined along a chamfered portion of the curved portion 50. The size of the openings, along with sufficient pressure may create microjets. The microjets break up into droplets at a certain distance after ejection from the opening, creating a spray. FIG. 4H shows another variation of the nozzle 52 having openings 30 defined along a portion which is reduced in its outer diameter relative to the remainder of the delivery component 20. This configuration gives the openings 30 some distance away from the nasal cavity target, allowing for the drug to spray outwardly in a wider range and allowing for the microjets to break up into droplets closer to the center axis of the delivery component 20. FIG. 4I shows an array of openings 30 in a more concentrated pattern on the nozzle 52, allowing the user to target a specific area of the nasal cavity more accurately. FIG. 4J shows another configuration with, e.g., two rows of openings 30 each having a dimeter of, e.g., 40 μm. Fewer total openings may allow for relatively easier micro-machining when manufacturing the nozzle 52.

Figure 4K:
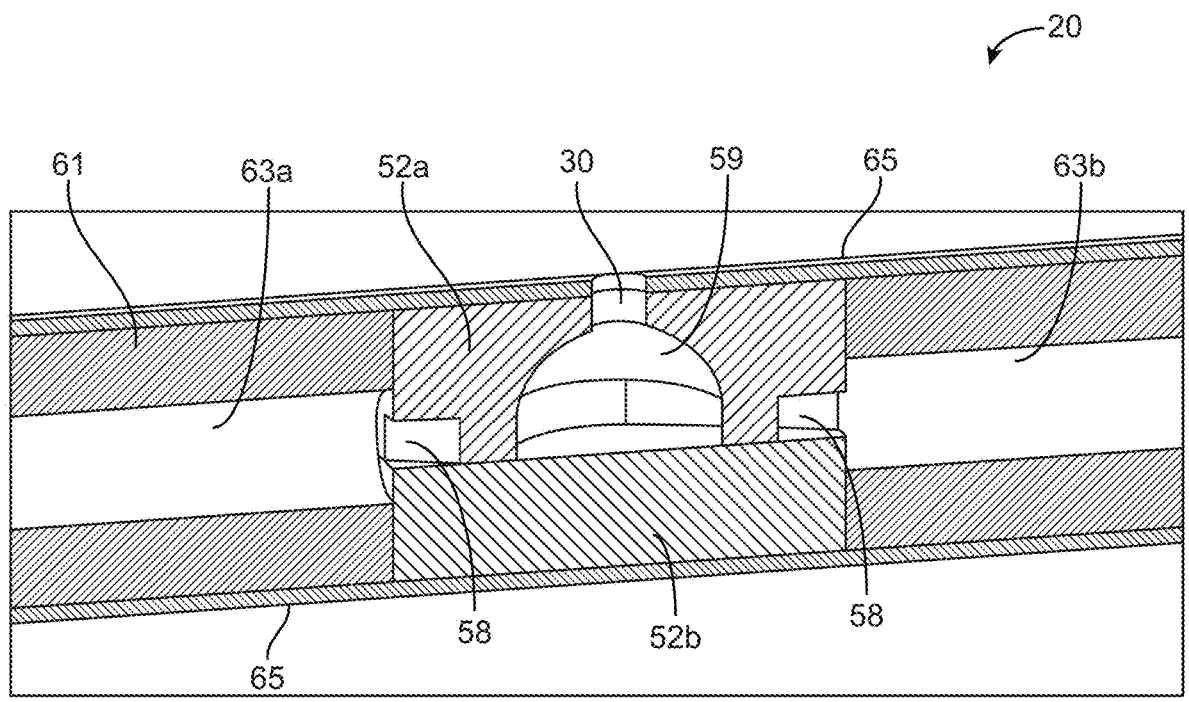
FIG. 4K show a cross-sectional perspective view of one variation illustrating how a nozzle assembly may be integrated with the delivery component.

Any of the described nozzle configurations herein may be incorporated into the distal end of the curved portion 50 or the distal end of the looped portion (if the curve is omitted), as described. In integrating the nozzle, the nozzle assembly may be positioned between the terminal ends of the tubing 61 which form the looped portion 50 so that the lumens 63a, 63b defined through the tube 61 are aligned with the nozzle bores 58 on either end of the nozzle. FIG. 4K shows a detailed cross-sectional perspective view of a nozzle assembly from FIGS. 4A and 4B where the upper and lower components 52a, 52b are attached to one another to form the swirl chamber 59 and angled nozzle bores 58 defined along either end of the nozzle assembly. The nozzle bores 58, which may present a flattened surface, may be aligned to respective ends of tubing 61 so that the ends may form a flush connection with the tubing 61. The fluid introduced into the lumen 63a, 63b may be forced into the respective nozzle bores 58 and into the swirl chamber 59 for subsequent atomization through opening 30.

The outer diameter of the nozzle assembly may be sized to form a flush coupling to the tubing 61 outer diameter. A sleeve 65 may also be formed or otherwise placed over the length of the tubing 61 and also over the nozzle assembly so that when the sleeve 65 is secured (e.g., heat shrink, melting, adhesives, etc.) to the outer surfaces of the underlying tubing 61 and nozzle, a seamless outer surface may be formed where the nozzle assembly forms an integral assembly with the tubing 61. The opening 30 of the nozzle may be formed through the sleeve 61 using any number of processing methods, e.g., machining, laser machining, etc.

Although the nozzle assembly is illustrated with a single opening, other variations may utilize multiple openings and/or any of the nozzle configurations shown and described herein in combination with the coupling process described.

Figure 5:
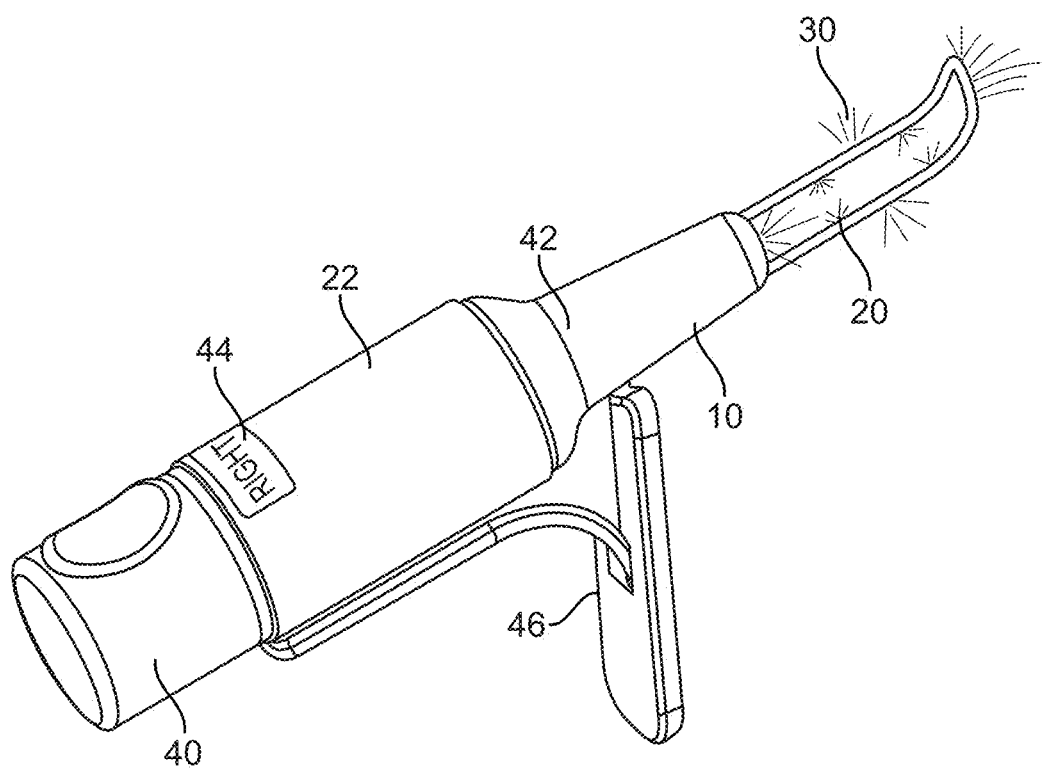
FIG. 5 shows a perspective view of a variation of the system of FIG. 3A with the loop having multiple holes.

FIG. 5 shows another variation of the nasal drug delivery system of FIG. 3A having multiple openings within the drug delivery component 20. Any number of openings may be used as desired depending on the procedure to be performed. The one or more openings 30 may be drilled by mechanical, optical, or thermal means and the openings 30 may cause the drug 24 to be dispersed as a stream or spray in various directions within the nasal cavity. Any number or all of these openings may be configured into any of the nozzle configurations as described herein.

FIGS. 6A to 6F show yet another variation of the nasal drug delivery system of FIG. 3A having a drug delivery component 20 with a dual lumen configuration. The dual lumen configuration may be used primarily for atomizing the drug. The drug delivery component 20 may have two lumens, an air lumen 66 and a liquid lumen 68, as shown in FIG. 6C. The dual-lumen system ensures that there is no mixing between the air and the liquid until the substances are about to be delivered to the nasal cavity through one or more openings 30. During use of the system, the device may pump a gas such as air through the air lumen 66 and the drug 24 through the liquid lumen 68. The pressurized lumens may cause both the air and the drug 24 to exit the one or more openings 30 simultaneously resulting in atomization of the drug 24. Alternatively, the sizes and shapes of the exit openings may be varied to optimize atomization while in other alternatives, the air and liquid lumens may be switched from that shown.

Alternatively, to atomize the drug, the guide container 22 may also be an aerosol canister which may contain a mixture of pressurized propellant and drug. In such embodiments, the atomized drug may be forced through the drug delivery component 20 and to exit through the one or more openings 30 in the drug delivery component 20.

FIGS. 7A and 7B show yet another variation of the nasal drug delivery system of FIG. 3A having a drug delivery component 20 with a center tube 70 which may be provided between the loop ends of the drug delivery component 20. As shown in FIG. 7B, the loop of the drug delivery component 20 may be closed to any flow of liquid or air and the center tube 70 may have a channel to deliver the drug. The channel may be in fluid communication with both an atomizer and the one or more openings of the loop. The atomizer may be a swirl atomizer, a plurality of micro holes, an ultrasonic membrane, impinging sprays, or any like as described herein. The drug may be pressurized when it is forced through the center tube 70 and through the hole 30 of the drug delivery component 20.

FIG. 8 shows yet another variation of the nasal drug delivery system of FIG. 3A having a series of relatively thin members 72 connecting ends of the loop to provide the loop with rigidity, enable flexibility, and allow for additional drug delivery locations. Members 72 can be made of any suitable material, including elastomers.

FIGS. 9A and 9B show yet another variation of the nasal drug delivery system. In this embodiment, the guide member 10 may function as the actuator 26. The guide member 10 may comprise finger grips 80 used for activation by the user so that the drug delivery component 20 may be slidably connected to the guide member 10 in such a way that a portion of the assembly is an integrated component where the guide member 10 and grips 80 are integrated as a singular component. In alternative variations, the grips 80 may be secured as separate components from the guide member 10. The guide member 10 may have a spring 76 loaded within for actuation of the system. The spring 76 may have a spray pump 74 at its proximal end and a spacer 78 at its distal end, the spacer 78 activating the spray pump 74 during actuation.

Similar to the previous embodiments, the drug delivery component 20 may be retracted into the guide in the resting position, as shown in FIG. 9A. During use, the user may place their fingers through the finger grips 80 and their thumb or palm on the proximal end of the guide housing 22. The user may then insert the guide member 10 into the nose. To activate the device, the user pushes the guide housing 22 towards the guide member, extending the drug delivery component 20 through the distal opening 16 of the guide member 10, as shown FIG. 9B. At the end of the actuation, the spacer 78 may activate the spray pump 74 and the drug may be delivered through the drug delivery component 20 to the target site. It should be understood that different length spacers can be used to change the length that the drug delivery component 20 extends past the distal end of the guide member 10. In other variations for actuating the device, the spray may be actuated by a button on the container or a pull-pin allowing the user to spray the target anatomy at any extension length.

Figure 10B:
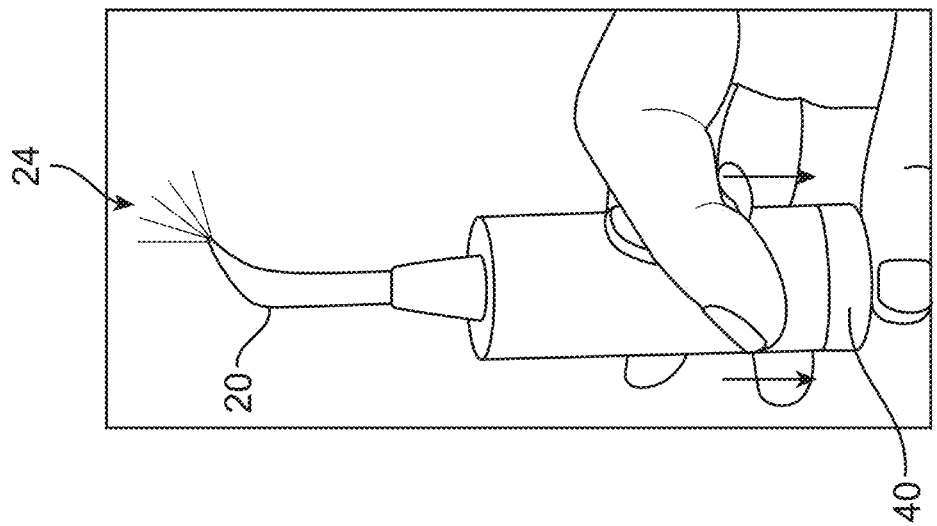
FIGS. 10A and 10B show side views of yet another variation of a nasal drug delivery system having a syringe configuration.
Figure 10A:
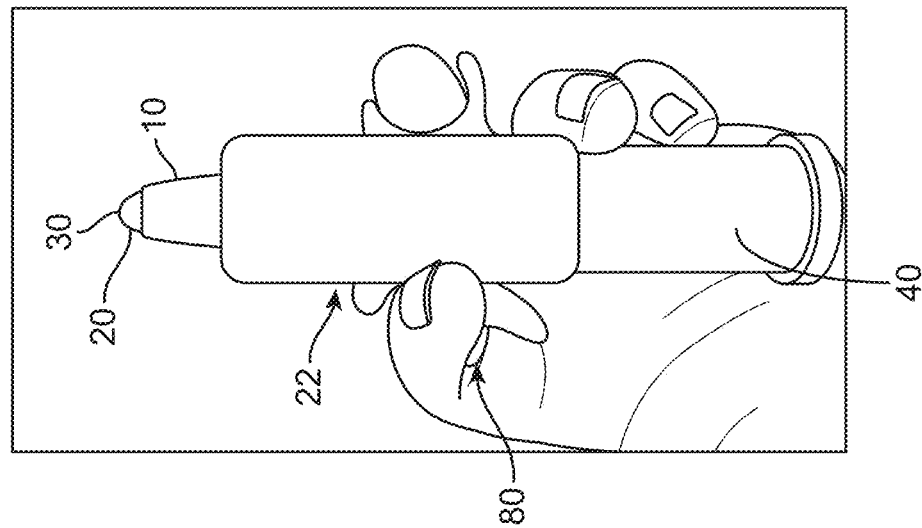

In yet another variation, the guide member 10, the drug delivery component 20, the actuator 26, and the guide housing 22 may be all housed in a syringe-like configuration, as shown in FIGS. 10A and 10B. This embodiment, which operates similarly to the embodiment of FIG. 9A above, may include finger grips 80 that are discontinuous (e.g., not in a circular shape) for alternative user access to the actuator 26.

Referring to FIGS. 11A to 11I, the drug delivery component 20 may have a preset shape. Different shapes allow the drug delivery component 20 to pass through the lower turbinate and into various target sites. For example, different shapes may allow for positioning of the component under the middle turbinate MT to access the middle meatus MM and beyond. The drug delivery component 20 may be flexible enough to pass through the lumen of the guide member 10 while still taking its preset shape after exiting the distal opening 16 of the guide member. The distal end of the drug delivery component 20 may be a larger or smaller diameter than the rest of the drug delivery component 20. The drug delivery component 20 may be made of a thermoplastic elastomer (e.g., 63 Shore D Pebax tubing), a thermoset elastomer (e.g., silicone), a thermoplastic (e.g., polypropylene), or a softer durometer material for greater patient comfort. The drug delivery component 20 may also be made of an annealed metal for malleability, or superelastic Nitinol to maintain flexibility while keeping its shape.

Figure 11A:
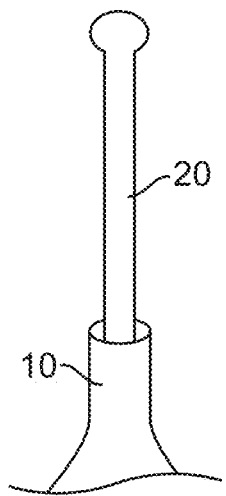
FIGS. 11A to 11K show schematic illustrations of various embodiments of the drug delivery component.
Figure 11B:
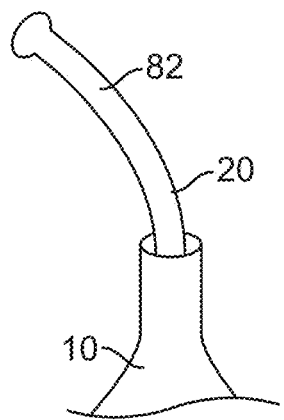
Figure 11C:
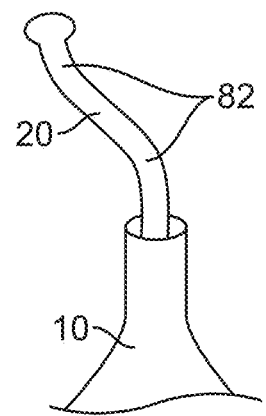

The drug delivery component 20 may be straight, as shown in FIG. 11A. The drug delivery component 20 may have a single bend 82, as shown in FIG. 11B. The drug delivery component 20 may have multiple bends 82, as shown in FIG. 11C. It should be understood that the angles of the drug delivery component 20 are not limited to the specific embodiments in FIGS. 11A to 11C. For example, the drug delivery component 20 may be angled according to variations in patient anatomy.

Figure 11D:
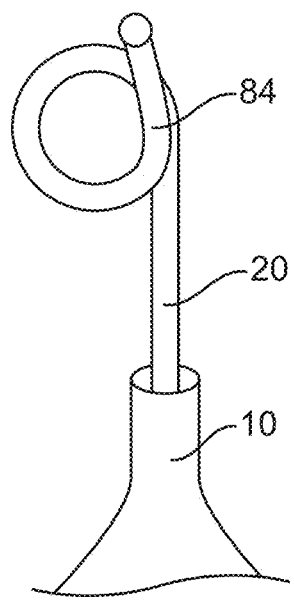
Figure 11E:
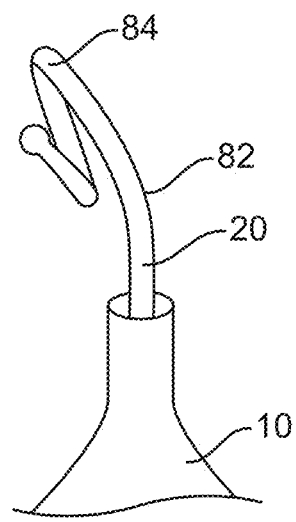

The drug delivery component 20 may have a pigtail shape 84, as shown in FIGS. 11D and 11E. The pigtail shape 84 may cover more area within the nasal cavity. By covering more area within the nasal cavity, the drug delivery component 20 may more widely distribute the drug if desired. The distal end of the pigtail 84 may be flexible enough to expand or contract to fit within the available space in the anatomy. The pigtail 84 may be a spiral, e.g., between 10 degrees to 720 degrees or higher. The pigtail shape 84 may also be atraumatic, allowing for patient comfort and safety during deployment of the system. As shown in FIG. 11E, the drug delivery component 20 may have a bend 82 to assist delivery to the target site. The bending of drug delivery component 20 allows the pigtail 84 to enter into the gap between the inferior and middle turbinates more easily.

Figure 11F:
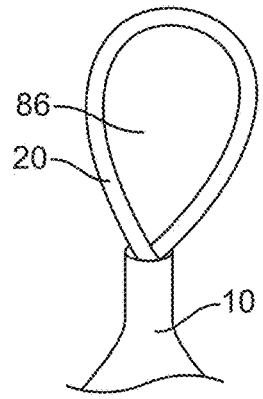
Figure 11G:
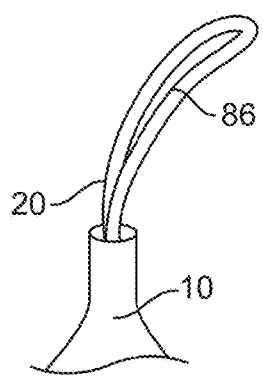

The drug delivery component 20 may have a loop shape 86, as shown in FIGS. 11F and 11G. The loop 86 may enter and exit the guide member 10 through the same or separate openings within the guide member 10. The loop 86 may be of a fixed length such that the loop 86 may be advanced into the middle meatus MM using a previously determined length. Alternatively, the loop 86 may be of an adjustable length, allowing the loop 86 to be advanced into the middle meatus MM at any custom length. As shown in FIG. 11G, the drug delivery component 20 may be angled to assist delivery to the target site. The angled component enters into the gap between the inferior and middle turbinates more easily. Alternatively, the loop 86 may twist to enter the middle meatus MM as it is advanced.

Figure 11H:
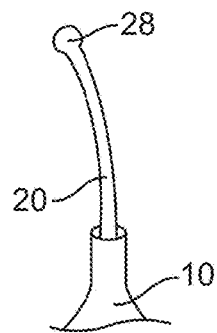
Figure 11I:
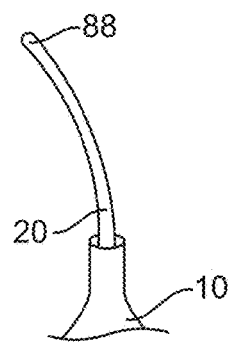

The drug delivery component 20 may have a bulbous tip 28 to ease insertion and prevent trauma, as shown in FIG. 11H. The bulbous tip 28 may be thin and round. Alternatively, the drug delivery component 20 may have a blunt end 88, as shown in FIG. 11I. The blunt end 88 may be a flat extrusion or nozzle as described above. In this embodiment, the drug delivery component 20 may not have a round cross-section.

Figure 11J:
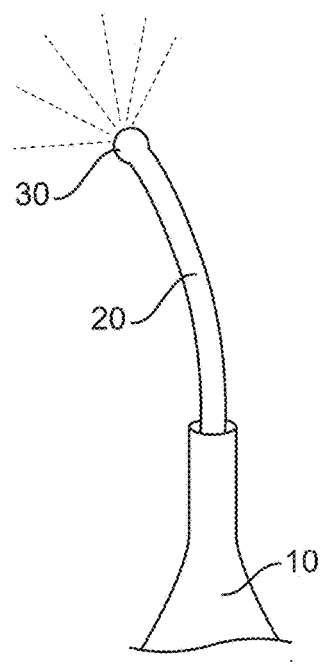
Figure 11K:
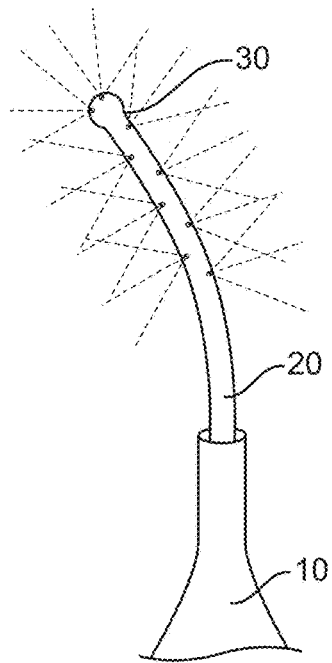

As previously described, the drug delivery component 20 may have a single opening 30 at its distal end, as shown in FIG. 11J. Alternatively, the drug delivery component 20 may have multiple openings 30 to spray the drug 24 to the nasal cavity, as shown in FIG. 11K. The spray may have a pattern that is in the shape of, e.g., a sphere, a hollow cone, a solid cone, mist, flat fan, or solid stream, etc. The particles may be, e.g., between 0.1 and 100 µm. In other embodiments, the device may be made without an atomizer and the drug can be delivered through the one or more openings 30 in liquid form.

Figure 11L:
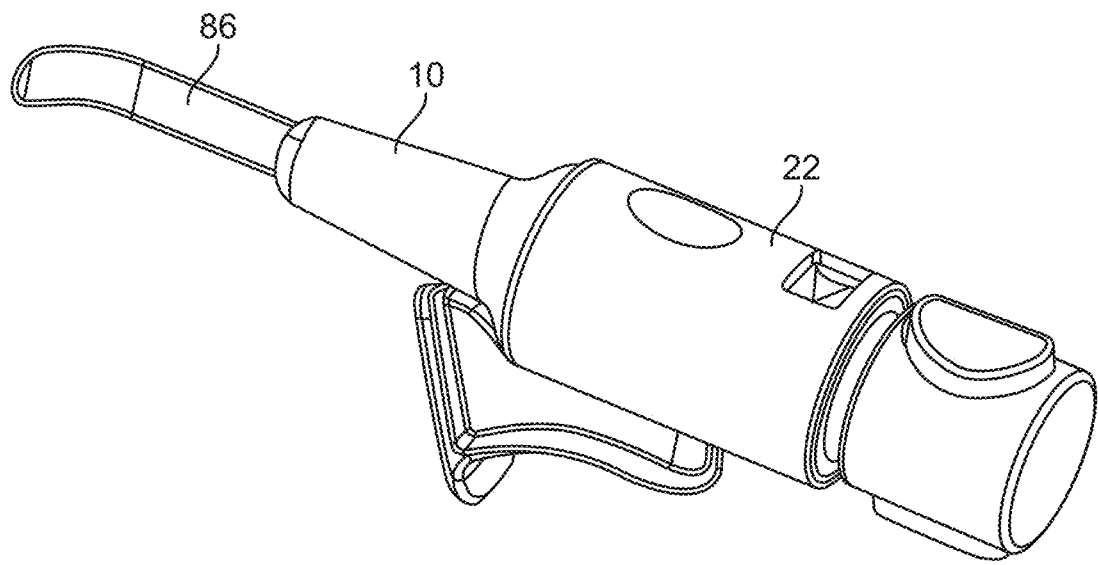
FIG. 11L shows a perspective view of another variation where the delivery component may be formed as a solid member.

In yet another variation, the loop may be configured as a solid component 86, as illustrated in the perspective view of FIG. 11L. The solid component 86 may incorporate the curved portion, as described herein, but rather than defining a space between the arm members, the entire member may be solid while still defining a flexible component. The component 86 may be retained within and deployed from the guide member 10 as previously described herein. Furthermore, because the component may be solid, the fluid channel may run through the center of the component 86 rather than along the perimeter.

Figure 11M:
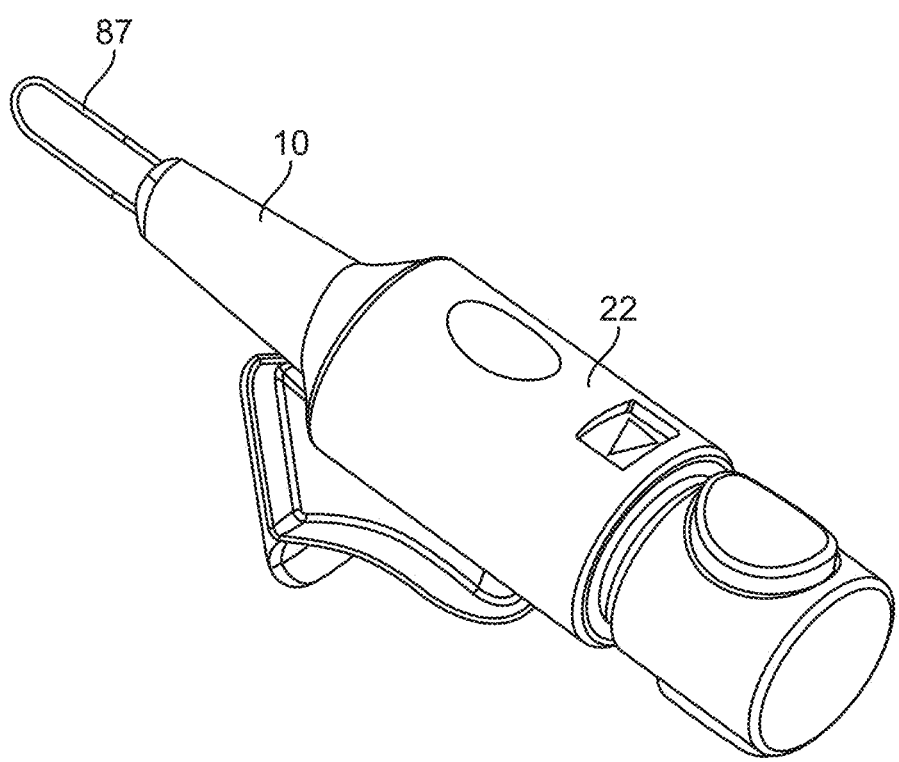
FIG. 11M shows a perspective view of yet another variation where the delivery component may be formed as a shortened member omitting the curved portion for insertion past the nasal valve.

Another variation is shown in the perspective view of FIG. 11M which illustrates a drug delivery component 87 which has a looped distal portion extending from two arm members but where the length of the component 87 is reduced and omits a curved distal portion. This variation may have a length which ranges from about 0.45 to 0.8 inch when extended from the guide member 10 so that when inserted into the nostril of a patient, the component 87 may extend just past the nasal valve for dispersion of a drug within the nasal cavity.

In other variations, the drug delivery component 20 may have a light, a fiber-optic, or the like at the distal end to allow for placement of the drug delivery component 20 to be confirmed by the user once it has reached the target site. In yet another variation, an endoscopic camera may be placed on the drug delivery component to allow the user to visualize the anatomy.

Figure 12A:
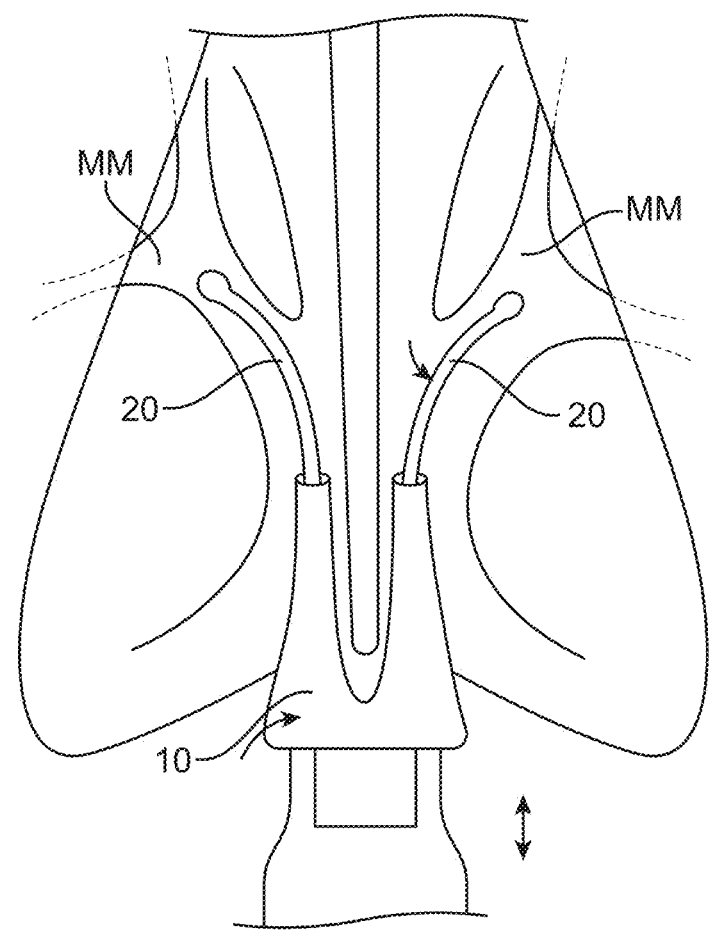
FIGS. 12A to 12F show different views of yet another variation of a nasal drug delivery system having two guide channels and two drug delivery components.
Figure 12B:
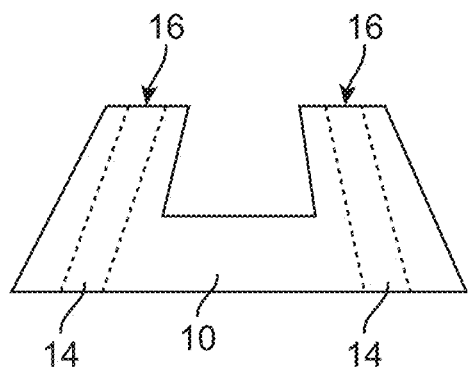
Figure 12C:
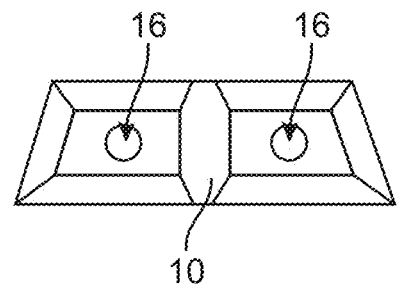
Figure 12D:
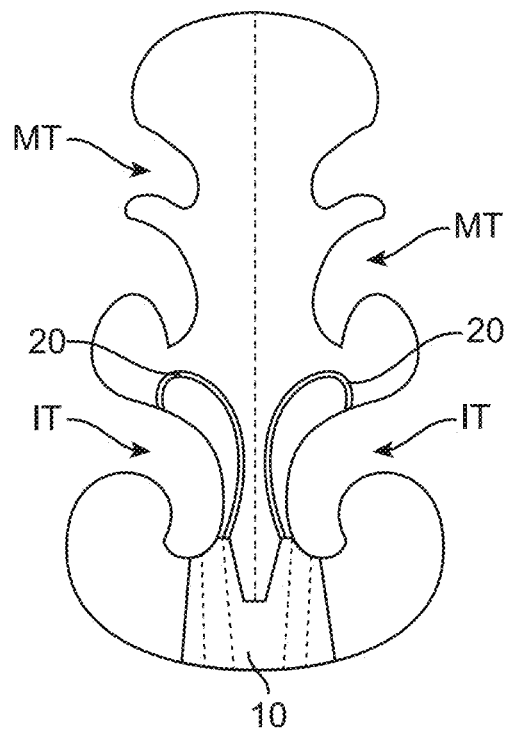
Figure 12E:
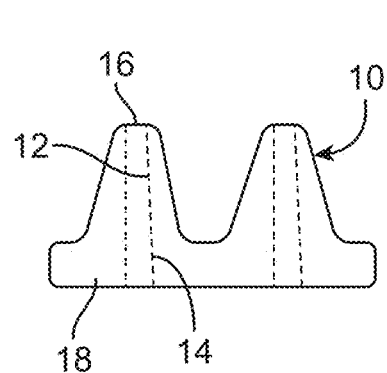
Figure 12F:
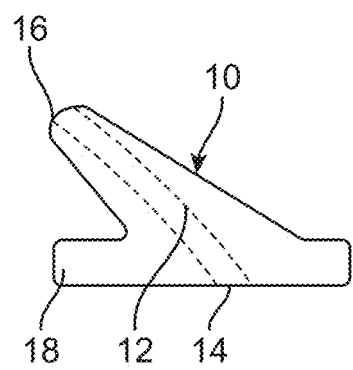

FIGS. 12A to 12F show yet another embodiment of the nasal drug delivery system. In this embodiment, the guide member 10 is designed to be inserted into two nostrils simultaneously. A drug delivery component 20 may have two separate components for simultaneous insertion into both guide channels 12. A single drug delivery component 20 may also be used for both guide channels 12. As shown in the side and top views of FIGS. 12B and 12C, the guide member 10 may be angled to more easily be inserted into the nose. Base 18 may be provided as an extension to guide member 10 for further anchoring to the patient's anatomy, as shown in FIGS. 12E and 12F.

Figure 13:
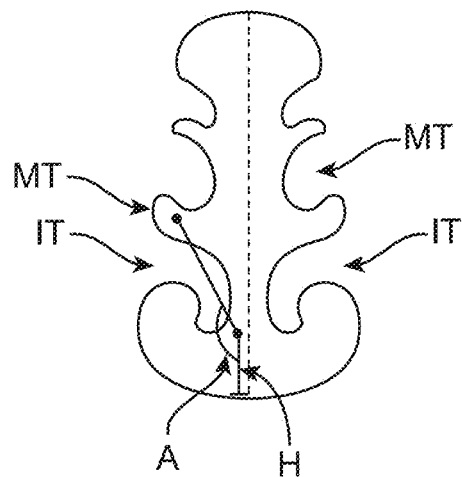
FIG. 13 to FIG. 17 show various methods of constructing the guide member.

The geometry of the guide may be determined by extrapolation from imaging data, such as from a volume computed tomography (CT) system, MRI, or ultrasound. A volume CT system may take an individual scanned image of the patient's nose to determine the shape and the size of the guide. As shown in FIG. 13, the geometry may be extracted from imaging data as a series of distances and angles in the anatomy of the nasal cavity (e.g., the distance from the opening of the nasal cavity or nare to the height H of the inferior turbinate, or the angle A from the superior portion of the inferior turbinate to the middle meatus). Alternatively, the geometry may be extracted by using segmentation software to reproduce a physical model of the nasal cavity up to the middle meatus. The software may be automated or manual. In all cases, measurements obtained may be used to generate either a mold for later casting the guide itself, for example, by 3D printing or other similar means.

Figure 14:
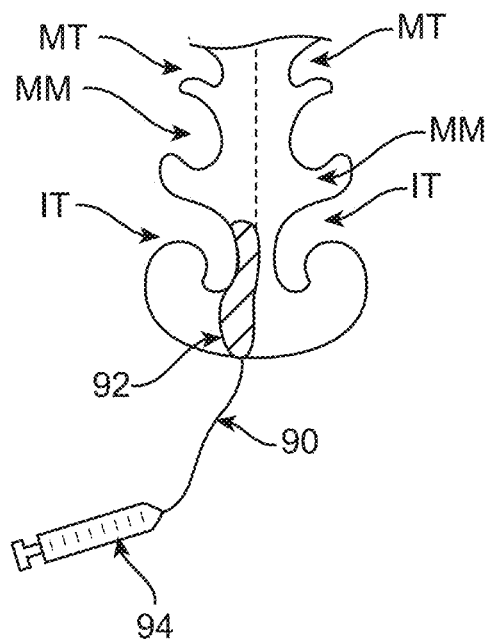

Alternatively, the geometry of the guide may be determined by custom molding. In this process, a hollow deformable container 92 may be first inserted into the nasal cavity, as shown in FIG. 14. The hollow container 92 may be an empty balloon. The hollow container 92 may be then filled with a molding substance (e.g., liquid, gel putty, 2-part silicone, or semi-solid) via a syringe 92 and a tubing 90. The molding substance may deform the container 92 to the shape of the nasal cavity, which may then harden. The container 92 may prevent the substance from flowing too far into the nasal cavity, preventing tissue contact with the substance. The hardened model of the nasal cavity may then be used to construct either the part itself or a mold of the part for later casting.

Figure 15:
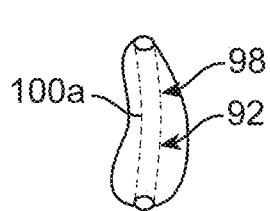
Figure 16:
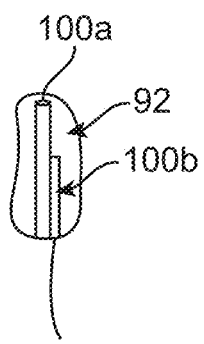
Figure 17:
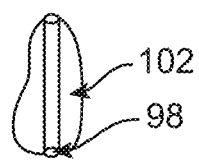

Referring to FIG. 15, the hollow portion(s) of the guide may also be created by inserting a space occupying tube 98 having a first lumen 100a in the desired position during the molding process. Referring to FIG. 16, the balloon 92 may contain a second lumen 100b which may serve as the channel through which the drug delivery component 20 may be delivered. The balloon may be placed with the assistance of a guide wire, under endoscopic visualization, or blindly. FIG. 17 shows another possibility for custom molding with the substance without a hollow container but using only a putty mold 102 instead. The space occupying tube 98 may be located within the part and may serve as the channel through which the drug delivery component 20 passes.

Alternatively, the geometry of the guide member may be determined by predetermined shapes and sizes. The length and orientation of the guide member may be constructed using predetermined size sets based on aggregates of measurements derived from imaging studies. The guide member may contain an articulating portion (e.g., a ball-in socket mechanism) to determine orientation and/or a telescoping portion to determine length of insertion. The guide member may be modular and consist of portions set to predetermined sizes and angles. The guide may also be flexible to deform to an individual patient's nasal cavity geometry. The guide may also be constructed of a malleable material to be set in the proper geometry.

The above embodiments may be adapted to other anatomical regions including, but not limited to: eustachian tubes, middle ear, adenoids, nasopharynx, nasolacrimal duct, olfactory cleft, infundibulum, sinuses, the olfactory region, the peripheral nervous, and the central nervous system. For example, the above embodiments may be made to deliver triptans, ergot alkaloids, or NSAIDs to the olfactory region to treat migraine. Insulin or Levodopa/Carbidopa may be delivered to the olfactory region to treat neurodegenerative disorders such as Alzheimer's and Parkinson's disease. Benzodiazepines or ketamine may be delivered to the olfactory region to treat psychiatric disorders such as depression, anxiety, and agitation. Benzodiazepines may be delivered to the olfactory region to treat seizures. Hormones may be delivered to the olfactory region to treat obesity. As such, the system may treat non-nasal disease states including, but not limited to: migraines, Alzheimer's disease, Parkinson's disease, psychiatric diseases, infections, neuralgias, pain, bleeding disorders, cardiovascular disease, autoimmune disease, diabetes mellitus, and infectious diseases. Embodiments may be adapted via adjustment of length, angle, and reach of both the guide member and the drug delivery components. The system may also be used to instead retrieve a culture from within the nasal cavity.

The disclosed invention herein is not limited to the embodiments and methods described, but may include any number of other applications and uses as well as applications in other regions of the body such as the vasculature. Modification of the above-described methods and devices for carrying out the invention, and variations of aspects of the invention that are obvious to those of skill in the arts are intended to be within the scope of this disclosure. Moreover, various combinations of aspects between examples are also contemplated and are considered to be within the scope of this disclosure as well.

What is claimed is:

1. A drug delivery system for delivering a substance into a subject, comprising:
   a housing for carrying the substance within;
   a guide member configured for insertion at least partially into a nasal cavity of the subject, the guide member having at least one lumen defined therethrough;
   a flexible member translatable through the at least one lumen of the guide member;
   a curved portion defined along the flexible member which forms a loop along the curved portion and having one or more openings defined along the loop at a distal end of the curved portion, wherein the curved portion extends at a predetermined curvature relative to the flexible member when the flexible member is translated from a retracted position to a deployed position and where the loop retains its configuration between the retracted position and the deployed position; and
   an alignment guide extending from the housing such that the alignment guide and guide member define an angle configured for positioning the curved portion within a predetermined position within the nasal cavity while the alignment guide and guide member remain stationary relative to one another as the flexible member is translated distally to the deployed position, wherein the guide member and flexible member are rotatable relative to the alignment guide for repositioning the curved portion.

2. The drug delivery system of claim 1, wherein the flexible member is detachable from the housing.

3. The drug delivery system of claim 1, wherein the one or more openings are in fluid communication with the substance.

4. The drug delivery system of claim 1, further comprising an actuator for ejecting the substance through the one or more openings.

5. The drug delivery system of claim 1, wherein the guide member and flexible member are rotatable about a longitudinal axis relative to the housing.

6. The drug delivery system of claim 5, wherein the curved portion is rotatable about the longitudinal axis such that the curved portion is positioned in an opposite direction.

7. The drug delivery system of claim 1, wherein the predetermined curvature defines a pigtail shape when in the deployed position.

8. The drug delivery system of claim 1, wherein the one or more openings have a nozzle configuration.

9. The drug delivery system of claim 1, wherein the alignment guide is configured for placement against an upper lip of the subject.

10. The drug delivery system of claim 1, wherein the angle between the alignment guide and guide member ranges between 110 and 120 degrees.

11. The drug delivery system of claim 10, wherein the angle between the alignment guide and guide member is about 112.5 degrees.

12. The drug delivery system of claim 1, wherein the housing is in fluid communication with the one or more openings through the flexible member.

13. The drug delivery system of claim 1, wherein the substance is a drug selected from the group consisting of cystalloids, corticosteroids, antihistamines, anticholinergics, antibiotics, antifungals, triptans, metabolites, NSAIDs, hormones, central nervous system agents, benzodiazepines, and anesthetics.

* * * * *